US006183988B1

(12) United States Patent
Bloch et al.

(10) Patent No.: US 6,183,988 B1
(45) Date of Patent: Feb. 6, 2001

(54) LEUKOCYTE-SPECIFIC PROTEIN AND GENE, AND METHODS OF USE THEREOF

(75) Inventors: Donald B. Bloch, Newton; Kenneth D. Bloch, Brookline, both of MA (US)

(73) Assignee: The General Hospital Corporation, Boston, MA (US)

( * ) Notice: Under 35 U.S.C. 154(b), the term of this patent shall be extended for 0 days.

(21) Appl. No.: 08/942,686

(22) Filed: Oct. 2, 1997

Related U.S. Application Data
(60) Provisional application No. 60/027,347, filed on Oct. 2, 1996.

(51) Int. Cl.[7] ............................. C12N 15/00; C12N 15/85; C12N 15/12

(52) U.S. Cl. ..................... 435/69.1; 435/320.1; 435/325; 536/23.1; 536/23.5

(58) Field of Search ................................. 536/23.5, 23.1; 435/320.1, 325, 69.1; 514/44

(56) References Cited

U.S. PATENT DOCUMENTS

| | | | |
|---|---|---|---|
| 4,631,211 | 12/1986 | Houghten | 428/35 |
| 4,833,092 | 5/1989 | Geysen | 436/501 |
| 5,194,392 | 3/1993 | Geysen | 436/518 |
| 5,480,971 | 1/1996 | Houghten et al. | 530/328 |

OTHER PUBLICATIONS

Ascoli, C.A., and Maul, G.G., "Identification of a Novel Nuclear Domain," *J. Cell Biol.* 112(5):785–795 (1991).
Bloch, D.B., et al., "Identification and Characterization of a Leukocyte–specific Component of the Nuclear Body," *J. Biol. Chem.* 271(46):29198–29204 (Nov. 15, 1996).
Borrow, J., et al., "Molecular Analysis of Acute Promyelocytic Leukemia Breakpoint Cluster Region on Chromosome 17," *Science* 249:1577–1580 (1990).
Brasch, K., and Ochs, R.L., "Nuclear Bodies (NBs): A Newly 'Rediscovered' Organelle," *Exp. Cell Res.* 202:211–223 (1992).
Carvalho, T., et al., "Targeting of Adenovirus E1A and E4–ORF3 Proteins to Nuclear Matrix–associated PML Bodies," *J. Cell Biol.* 131(1):45–56 (Oct. 1995).
Daniel, M.T., et al., "PML Protein Expression in Hematopoietic and Acute Promyelocytic Leukemia Cells," *Blood* 82(6):1858–1867 (1993).
Dent, A.L., et al., "LYSP100–Associated Nuclear Domains (LANDs): Description of a New Class of Subnuclear Structures and Their Relationship to PML Nuclear Bodies," *Blood* 88(4):1423–1436 (Aug. 15, 1996).
de Thé, H., et al., "The t(15;17) translocation of acute promyelocytic leukaemia fuses the retinoic acid receptor α gene to a novel transcribed locus," *Nature* 347:558–561 (1990).
Dingwall, C., and Laskey, R.A., "Nuclear targeting sequences—a consensus?," *Trends in Biochem. Sci.* 16:478–481 (1991).

Doucas, V., et al., "Adenovirus replication is coupled with the dynamic properties of the PML nuclear structure," *Genes & Develop.* 10:196–207 (Jan. 15, 1996).
Dyck, J.A., et al., "A Novel Macromolecular Structure Is a Target of the Promyelocyte–Retinoic Acid Receptor Oncoprotein," *Cell* 76:333–343 (1994).
Evans, J., et al., "PBC 95K, A 95–Kilodalton Nuclear Autoantigen in Primary Biliary Cirrhosis," *Arthritis & Rheum.* 34(6):731–736 (1991).
Frohman, M.A., et al., "Rapid production of full–length cDNAs from rare transcripts: Amplification using a single gene–specific oligonucleotide primer," *Proc. Natl. Acad. Sci. USA* 85:8998–9002 (1988).
Gentz, R., et al., "Bioassay for trans–activation using purified human immunodeficiency virus tat–encoded protein: Trans–activation requires mRNA synthesis," *Proc. Natl. Acad. Sci. USA* 86:821–824 (1989).
Guldner, H.H., et al., "IFN Enhance Expression of Sp100, An Autoantigen in Primary Biliary Cirrhosis," *J. Immunol.* 149(12):4067–4073 (1992).
Haynes, S.R., et al., "The bromodomain: a conserved sequence found in human, Drosophila and yeast proteins," *Nucl. Acids Res.* 20(10):2603 (1992).
Hochuli, E., et al., "New Metal Chelate Adsorbent Selective for Proteins and Peptides Containing Neighbouring Histidine Residues," *J. Chromatogr.* 411:177–184 (1987).
Kakizuka, A., et al., "Chromosomal Translocation t(15;17) in Human Acute Promyelocytic Leukemia Fuses RARα with a Novel Putative Transcription Factor, PML," *Cell* 66:663–674 (1991).
Koken, M.H.M., et al., "The t(15;17) translocation alters a nuclear body in a retinoic acid–reversible fashion," *EMBO J.* 13(5):1073–1083 (1994).
Koken, M.H.M., et al., "The PML growth–suppressor has an altered expression in human oncogenesis," *Oncogene* 10:1315–1324 (Apr. 6, 1995).
Koken, M.H.M., et al., "A $C_4HC_3$ zinc finger motif," *C.R. Acad. Sci. Paris, Sci. de la Vie* 318(7):733–739 (Jul. 1995).
Korioth, F., et al., "Molecular Characterization of NDP52, A Novel Protein of the Nuclear Domain 10, Which Is Redistributed upon Virus Infection and Interferon Treatment," *J. Cell Biol.* 130(1):1–13 (Jul. 1995).

(List continued on next page.)

*Primary Examiner*—John L. LeGuyader
*Assistant Examiner*—Dave Trong Nguyen
(74) *Attorney, Agent, or Firm*—Sterne, Kessler, Goldstein & Fox P.L.L.C.

(57) ABSTRACT

The present invention is directed to a leukocyte-specific gene Sp140 and its associated protein. Since it has structural analogies to other regulatory proteins and is localized in the nuclear body of certain cell types, Sp140 may be a transcription regulator involved in the body's interaction with viruses and in promyelocytic leukemia. The Sp140 gene can be used in gene therapy for treating certain viral diseases, autoimmune disorders and cancers, while the Sp140 protein may be useful as a diagnostic and prognostic marker in the analysis of certain autoimmune disorders.

7 Claims, 12 Drawing Sheets

OTHER PUBLICATIONS

Lanotte, M., et al., "NB4, a Maturation Inducible Cell Line With t(15;17) Marker Isolated From a Human Acute Promyelocytic Leukemia (M3)," *Blood* 77(5):1080–1086 (1991).

Longo, L., et al., "Rearrangements and Aberrant Expression of the Retinoic Acid Receptor α Gene in Acute Promyelocytic Leukemias," *J. Exp. Med.* 172:1571–1575 (1990).

Lygerou, Z., et al., "The yeast BDF1 gene encodes a transcription factor involved in the expression of a broad class of genes including snRNAs," *Nucl. Acids Res.* 22(24):5332–5340 (1994).

Maul, G.G., et al., "Modification of discrete nuclear domains induced by herpes simplex virus type 1 immediate early gene 1 product (ICPO)," *J. Gen. Virol.* 74:2679–2690 (1993).

Maul, G.G., and Everett, R.D., "The nuclear location of PML, a cellular member of the $C_3HC_4$ zinc–binding domain protein family, is rearranged during herpes simplex virus infection by the $C_3HC_4$ viral protein ICPO," *J. Gen. Virol.* 75:1223–1233 (1994).

Puvion–Dutilleul, F., et al., "Adenovirus Infection Induces Rearrangements in the Intranuclear Distribution of the Nuclear Body–Associated PML Protein," *Exp. Cell Res.* 218:9–16 (May 1995).

Robbins, J., et al., "Two Interdependent Basic Domains in Nucleoplasmin Nuclear Targeting Sequence: Identification of a Class of Bipartite Nuclear Targeting Sequence," *Cell* 64:615–623 (1991).

Ruchaud, S., et al., "Two distinctly regulated events, priming and triggering, during retinoid–induced maturation and resistance of NB4 promyelocytic leukemia cell line," *Proc. Natl. Acad. Sci. USA* 91:8428–8432 (1994).

Silver, P.A., "How Proteins Enter the Nucleus," *Cell* 64:489–497 (1991).

Smith, D.B., and Johnson, K.S., "Single–step purification of polypeptides expressed in *Escherichia coli* as fusions with glutathione S–transferase," *Gene* 67:31–40 (1988).

Staunton, D.E., et al., "Primary Structure of ICAM–1 Demonstrates Interaction between Members of the Immunoglobulin and Integrin Supergene Families," *Cell* 52:925–933 (1988).

Sternsdorf, T., et al., "Two Nuclear Dot–Associated Proteins, PML and Sp100, are Often Co–Autoimmunogenic in Patients with Primary Biliary Cirrhosis," *Scand. J. Immunol.* 42:257–268 (Aug. 1995).

Szostecki, C., et al., "Isolation and Characterization of cDNA Encoding a Human Nuclear Antigen Predominantly Recognized by Autoantibodies from Patients with Primary Biliary Cirrhosis," *J. Immunol.* 145(12):4338–4347 (1990).

Szostecki, C., et al., "Autoantibodies to the Nuclear Sp100 Protein in Primary Biliary Cirrhosis and Associated Diseases: Epitope Specificity and Immunoglobulin Class Distribution," *Scand. J. Immunol.* 36:555–564 (1992).

Tamkun, J.W., et al., "brahma: A Regulator of Drosophila Homeotic Genes Structurally Related to the Yeast Transcriptional Activator SNF2/SWI2," *Cell* 68:561–572 (1992).

Warrell, Jr., R.P., "Retinoid Resistance in Acute Promyelocytic Leukemia: New Mechanisms, Strategies, and Implications," *Blood* 82(7):1949–1953 (1993).

Weis, K., et al., "Retinoic Acid Regulates Aberrant Nuclear Localization of PML–RARα in Acute Promyelocytic Leukemia Cells," *Cell* 76:345–356 (1994).

Wilson, I.A., et al., "The Structure of an Antigenic Determinant in a Protein," *Cell* 37:767–778 (1984).

Xie, K., et al., "Nuclear Dot Antigens May Specify Transcriptional Domains in the Nucleus," *Mol. Cell. Biol.* 13(10):6170–6179 (1993).

Bloch, D.B. et al., "Autoantigens and the Nuclear Body," *Arthritis & Rheumatism* 39(9):S43, Abstract No. 99 (Sep. 1996).

Database EMBL, entry HS483220, Accession No. H66483, created and last updated Oct. 21, 1995.

Database EMBL, entry HS484219, Accession No. H66484, created and last updated Oct. 21, 1995.

Database EMBL, entry HS857357, Accession No. G25857, created and last updated Jun. 6, 1996.

Database EMBL, entry HSG27974, Accession No. G27974, created and last updated Jul. 1, 1996.

DS Charnock–Jones et al (1994) J Biotechnology 35: 205–215.*

JC Venter et al (1992) Trends in Biotechnology 10: 8–11.*

IM Verma et al (1997) Nature 389: 239–242.*

WF Anderson (1998) Nature 392: 25–30.*

Hillier et al (1995) Gen Bank accession No. H66484.*

Hillier et al (1995) GenBank accession No. H66483.*

S Kadereit et al (1993) J Biol Chem 268: 24432–24441.*

* cited by examiner

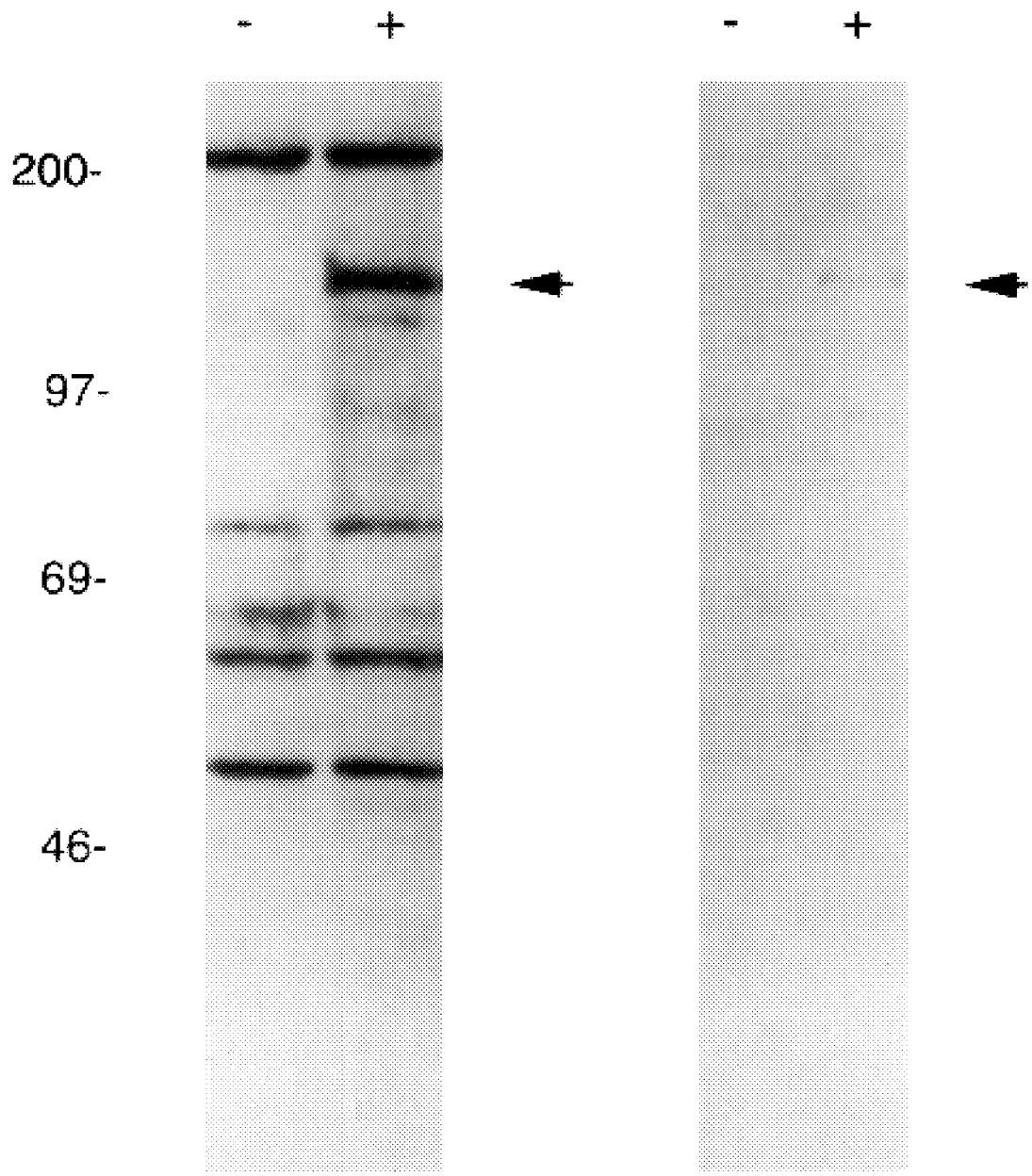

```
GTGCTCTTTG ACTGAGCACC GAGGGGCAGT TGGCAGCTTC ACCTCAGAGC TGCAGGAAGG         60

AACGGGGCAG TGAAAATCGA ATCGGGTGTG ATCCTAGGCC AAGCTC ATG GCC CAG           115
                                                  Met Ala Gln
                                                   1

CAG GGC CAG CAG GGG CAA ATG GCA AGT GGA GAC AGC AAT CTC AAC TTC          163
Gln Gly Gln Gln Gly Gln Met Ala Ser Gly Asp Ser Asn Leu Asn Phe
     5              10                  15

AGG ATG GTC GCA GAG ATC CAG AAC GTA GAG GGT CAG AAC CTG CAG GAG          211
Arg Met Val Ala Glu Ile Gln Asn Val Glu Gly Gln Asn Leu Gln Glu
 20              25              30              35

CAG GTT TGC CCT GAG CCC ATT TTC AGG TTC TTC AGA GAA AAC AAG GTG          259
Gln Val Cys Pro Glu Pro Ile Phe Arg Phe Phe Arg Glu Asn Lys Val
             40              45              50

GAG ATT GCA AGT GCA ATA ACA AGG CCA TTT CCT TTC CTT ATG GGC CTC          307
Glu Ile Ala Ser Ala Ile Thr Arg Pro Phe Pro Phe Leu Met Gly Leu
         55              60              65

CGA GAC CGC TCC TTC ATC TCC GAG CAG ATG TAT GAA CAT TTT CAA GAA          355
Arg Asp Arg Ser Phe Ile Ser Glu Gln Met Tyr Glu His Phe Gln Glu
         70              75              80

GCT TTT AGA AAC CTG GTC CCA GTG ACA AGA GTG ATG TAT TGT GTA CTC          403
Ala Phe Arg Asn Leu Val Pro Val Thr Arg Val Met Tyr Cys Val Leu
     85              90              95

AGT GAA CTG GAG AAG ACA TTT GGC TGG TCA CAT CTG GAA GCA TTG TTC          451
Ser Glu Leu Glu Lys Thr Phe Gly Trp Ser His Leu Glu Ala Leu Phe
100             105             110             115

AGC AGG ATT AAC CTG ATG GCC TAT CCT GAT TTA AAC GAG ATT TAC AGA          499
Ser Arg Ile Asn Leu Met Ala Tyr Pro Asp Leu Asn Glu Ile Tyr Arg
            120             125             130

AGC TTC CAG AAT GTA TGC TAT GAA CAC TCA CCT CTC CAA ATG AAT AAT          547
Ser Phe Gln Asn Val Cys Tyr Glu His Ser Pro Leu Gln Met Asn Asn
            135             140             145

GTA AAC GAT TTA GAA GAT AGA CCC AGA TTA CTA CCA TAT GGT AAA CAA          595
Val Asn Asp Leu Glu Asp Arg Pro Arg Leu Leu Pro Tyr Gly Lys Gln
            150             155             160

GAG AAC AGC AAT GCC TGT CAT GAA ATG GAT GAT ATA GCA GTG CCT CAG          643
Glu Asn Ser Asn Ala Cys His Glu Met Asp Asp Ile Ala Val Pro Gln
```

FIG.2A

```
            Glu Asn Ser Asn Ala Cys His Glu Met Asp Asp Ile Ala Val Pro Gln
                165                 170                 175

GAA GCC TTG AGC TCC TCG GCA AGG TGT GAG CCA GGT TTC TCT TCA GAG    691
            Glu Ala Leu Ser Ser Ser Ala Arg Cys Glu Pro Gly Phe Ser Ser Glu
            180                 185                 190                 195

TCT TGT GAG CAG TTA GCT CTC CCA AAG GCT GGT GGA GGA GAT GCT GAA    739
            Ser Cys Glu Gln Leu Ala Leu Pro Lys Ala Gly Gly Gly Asp Ala Glu
                                200                 205                 210

GAT GCA CCC AGC CTA CTA CCA GTG TCC TGT AAA CTT GCT ATA CAA ATA    787
            Asp Ala Pro Ser Leu Leu Pro Val Ser Cys Lys Leu Ala Ile Gln Ile
                            215                 220                 225

GAT GAA GGA GAA TCA GAA GAA ATG CCC AAG TTA CTG CCT TAT GAT ACA    835
            Asp Glu Gly Glu Ser Glu Glu Met Pro Lys Leu Leu Pro Tyr Asp Thr
                        230                 235                 240

GAA GAG ACC TTT GAT CTA AAA ACT CCC CAA GTC ACT AAT GAA GGA GAA    883
            Glu Glu Thr Phe Asp Leu Lys Thr Pro Gln Val Thr Asn Glu Gly Glu
                    245                 250                 255

CCA GAG AAG GGG CTC TGT CTA CTA CCA GGT GAA GGA GAA GAG GGC AGT    931
            Pro Glu Lys Gly Leu Cys Leu Leu Pro Gly Glu Gly Glu Glu Gly Ser
                260                 265                 270                 275

GAT GAC TGT TCG GAA ATG TGT GAT GGA GAA GAG CGC CAG GAA GCC TCT    979
            Asp Asp Cys Ser Glu Met Cys Asp Gly Glu Glu Arg Gln Glu Ala Ser
                            280                 285                 290

AGC TCC CTA GCA AGA CGT GGG TCA GTG TCT AGT GAA CTA GAA AAT CAC    1027
            Ser Ser Leu Ala Arg Arg Gly Ser Val Ser Ser Glu Leu Glu Asn His
                        295                 300                 305

CCA ATG AAT GAA GAA GGA GAA TCA GAA GAG CTT GCT TCT AGC CTG CTA    1075
            Pro Met Asn Glu Glu Gly Glu Ser Glu Glu Leu Ala Ser Ser Leu Leu
                    310                 315                 320

TAT GAT AAT GTA CCA GGA GCG GAG CAA TCA GCA TAT GAA AAT GAG AAG    1123
            Tyr Asp Asn Val Pro Gly Ala Glu Gln Ser Ala Tyr Glu Asn Glu Lys
                325                 330                 335

TGT TCC TGT GTC ATG TGT TTC TCA GAA GAG GTG CCA GGA AGC CCA GAA    1171
            Cys Ser Cys Val Met Cys Phe Ser Glu Glu Val Pro Gly Ser Pro Glu
            340                 345                 350                 355

GCA AGG ACG GAA AGT GAT CAA GCG TGT GGC ACA ATG GAT ACT GTG GAT    1219
            Ala Arg Thr Glu Ser Asp Gln Ala Cys Gly Thr Met Asp Thr Val Asp
                            360                 365                 370

ATT GCA AAC AAC TCC ACT TTG GGA AAA CCC AAG AGG AAA AGA AGA AAA    1267
            Ile Ala Asn Asn Ser Thr Leu Gly Lys |Pro Lys Arg Lys Arg Arg Lys|
                        375                 380                 385
```

FIG.2B

| | |
|---|---|
| AAG AGG GGG CAT GGC TGG AGC AGA ATG AGA ATG AGA AGG CAG AAA AAC<br><u>Lys Arg Gly His Gly Trp Ser Arg Met Arg Met Arg Arg</u> Gln Lys Asn<br>390                    395                  400 | 1315 |
| AGC CAA CAA AAT GAT AAT AGC AAA GCC GAC GGC CAG GTG GTC TCC AGT<br>Ser Gln Gln Asn Asp Asn Ser Lys Ala Asp Gly Gln Val Val Ser Ser<br>405                   410                  415 | 1363 |
| GAA AAG AAG GCG AAC GTG AAT CTG AAA GAC CTT TCC AAG ATT AGG GGG<br>Glu Lys Lys Ala Asn Val Asn Leu Lys Asp Leu Ser Lys Ile Arg Gly<br>420                   425                  430                  435 | 1411 |
| AGA AAG AGA GGC AAA CCT GGA ACC CGC TTC ACT CAG AGT GAC AGA GCT<br>Arg Lys Arg Gly Lys Pro Gly Thr Arg Phe Thr Gln Ser Asp Arg Ala<br>440                   445                  450 | 1459 |
| GCA CAG AAA AGA GTC CGA TCA AGA GCT TCA AGA AAG CAC AAA GAT GAA<br>Ala Gln Lys Arg Val Arg Ser Arg Ala Ser Arg Lys His Lys Asp Glu<br>455                   460                  465 | 1507 |
| ACT GTG GAT TTT AAG GCT CCT TTG CTT CCA GTG ACC TGT GGT GGG GTG<br>Thr Val Asp Phe Lys Ala Pro Leu Leu Pro Val Thr Cys Gly Gly Val<br>470                   475                  480 | 1555 |
| AAG GGA ATT TTA CAT AAG AAG AAA TTG CAG CAA GGA ATC TTG GTG AAG<br>Lys Gly Ile Leu His Lys Lys Lys Leu Gln Gln Gly Ile Leu Val Lys<br>485                   490                  495 | 1603 |
| TGT ATA CAG ACT GAG GAT GGA AAA TGG TTC ACC CCC ACG GAA TTT GAA<br>Cys Ile Gln Thr Glu Asp Gly Lys Trp Phe Thr Pro Thr Glu Phe Glu<br>500                   505                  510                  515 | 1651 |
| ATC AAA GGA GGC CAT GCA AGA TCA AAG AAC TGG AGG CTG AGT GTG CGC<br>Ile Lys Gly Gly His Ala Arg Ser Lys Asn Trp Arg Leu Ser Val Arg<br>520                   525                  530 | 1699 |
| TGT GGC GGG TGG CCC CTA CGA TGG CTG ATG GAG AAT GGA TTT CTG CCT<br>Cys Gly Gly Trp Pro Leu Arg Trp Leu Met Glu Asn Gly Phe Leu Pro<br>535                   540                  545 | 1747 |
| GAT CCT CCA AGA ATA CGT TAC AGG AAA AAA AGA ATA CTG AAG TCT<br>Asp Pro Pro Arg Ile Arg Tyr Arg Lys Lys Lys Arg Ile Leu Lys Ser<br>550                   555                  560 | 1795 |
| CAA AAC AAT AGC TCA GTT GAC CCT TGT ATG AGA AAC CTG GAT GAG TGT<br>Gln Asn Asn Ser Ser Val Asp Pro Cys Met Arg Asn Leu Asp Glu (Cys)<br>565                   570                  575 | 1843 |
| GAG GTG TGC CGG GAC GGA GGG GAG CTG TTC TGT TGC GAC ACT TGT TCA<br>Glu Val (Cys) Arg Asp Gly Gly Glu Leu Phe Cys (Cys) Asp Thr (Cys) Ser<br>580                   585                  590                  595 | 1891 |
| AGA GTC TTC CAT GAG GAC TGT CAC ATC CCG CCT GTG GAA GCT GAG AGG<br>Arg Val Phe (His) Glu Asp (Cys) His Ile Pro Pro Val Glu Ala Glu Arg<br>600                   605                  610 | 1939 |

FIG.2C

```
ACC CCG TGG AAT TGC ATC TTC TGC AGG ATG AAG GAG TCT CCG GGA AGC        1987
Thr Pro Trp Asn Cys Ile Phe Cys Arg Met Lys Glu Ser Pro Gly Ser
            615         620                 625

CAA CAG TGT TGT CAG GAA TCT GAG GTC CTG GAG AGG CAG ATG TGT CCT        2035
Gln Gln Cys Cys Gln Glu Ser Glu Val Leu Glu Arg Gln Met Cys Pro
        630             635             640

GAG GAA CAG TTG AAA TGT GAG TTC CTC CTC TTG AAA GTC TAT TGC TGT        2083
Glu Glu Gln Leu Lys Cys Glu Phe Leu Leu Leu Lys Val Tyr Cys Cys
        645             650             655

TCT GAG AGC TCC TTT TTT GCC AAG ATT CCA TAC TAT TAT TAT ATT AGA        2131
Ser Glu Ser Ser Phe Phe Ala Lys Ile Pro Tyr Tyr Tyr Tyr Ile Arg
660             665             670             675

GAG GCG TGT CAA GGC CTG AAG GAG CCC ATG TGG TTG GAT AAA ATC AAG        2179
Glu Ala Cys Gln Gly Leu Lys Glu Pro Met Trp Leu Asp Lys Ile Lys
            680             685             690

AAA AGG CTG AAT GAG CAC GGT TAC CCC CAA GTG GAG GGG TTT GTA CAA        2227
Lys Arg Leu Asn Glu His Gly Tyr Pro Gln Val Glu Gly Phe Val Gln
        695             700             705

GAC ATG CGC CTC ATC TTC CAG AAC CAC AGG GCC TCT TAC AAG TAC AAG        2275
Asp Met Arg Leu Ile Phe Gln Asn His Arg Ala Ser Tyr Lys Tyr Lys
        710             715             720

GAT TTT GGC CAA ATG GGA TTT AGA CTG GAG GCT GAG TTT GAG AAG AAT        2323
Asp Phe Gly Gln Met Gly Phe Arg Leu Glu Ala Glu Phe Glu Lys Asn
725             730             735

TTC AAG GAA GTG TTT GCT ATT CAG GAA ACA AAT GGG AAC AAT                2365
Phe Lys Glu Val Phe Ala Ile Gln Glu Thr Asn Gly Asn Asn
740             745             750

TGACTGGATT AGTGGATGCT GAAAGCATTC AGCAAATGGC ACCCTAAAAT ATGCCGCTGG      2425

TTTGCCACTG ACTTCAAAAT GAGGTCACTT GGGCACAGCA CATGCAGGGA GGGGCTTTTC      2485

TCTGAGCCTC CTTCATCTGC CCAAAGACAA ATCCTCAAAA GGAAATTCAA TCATCATGAA      2545

TCACAACCCC AAGTATCTCA TCAGCCAGGG AAGAGTAAGT GGGATCACAG GAAGGATGT       2605

TGGCAGCGAC ACCATCCCAT ACAGGCTCTT ACCTCTTCTC CTGAGGGCTG CTCCAGACAA      2665

CATTTATTAC CCAGAAGACC TTTTGTCTGA AAACCAGCCA AGCTTTATTC AGGACACACT      2725

TCTTGCCTTC ACTTTCCCAC TTCCGTGGCC ACCTCCATGC AGAAGCCCTA AGCCCACATT      2785

CTTTCAATAG CTCACGGTGG TGCATGAGTG TCCATCATCT GACTCTTCTC GGAGTCTCAT      2845

ATTTTGTGGG ACTCCTGTGC AAACATATGT TATTAAAATT TTTTTCCTCC TGTAAAGGAA      2905
```

FIG.2D

```
Sp140   29  EGQNLQEQVCPEPIFRFFRENKVEIASAITRPFPFLMGLRDRSFISEQMYEHFQEAFRNL   88
            E Q + +++   + +F+ F+ NKVEI++AI + FPFL GLRDR  I+ +M+E  Q++ RNL
Sp100   40  EDQGVDDRLLYDIVFKHFKRNKVEISNAIKKTFPFLEGLRDRDLITNKMFEDSQDSCRNL   99

Sp140   89  VPVTRVMYCVLSELEKTFGWSHLEALFSRINLMAYPDLNEIYRSFQNVCYEHSPLQMNNV  148
            VPV RV+Y VLSELEKTF     LEALFS +N+  YPDL  IY+ F+NV ++  PLQ +
Sp100  100  VPVQRVVYNVLSELEKTFNLPVLEALFSDVNMQEYPDLIHIYKGFENVIHDKLPLQESEE  159

Sp140  149  NDLEDRPRL  157
             + E+R L
Sp100  160  EEREERSGL  168
```

FIG. 2E

```
Sp140   684 LKEPMWLDKIKKRLNEHGYPQVEGFVQDMRLIFQN 718
            +KEPM L   I K+LN+   Y  +E F +D+RL+F+N
BDF1    357 VKEPMDLGTIAKKLNDWQYQTMEDFERDVRLVFKN 391
```

FIG.2F

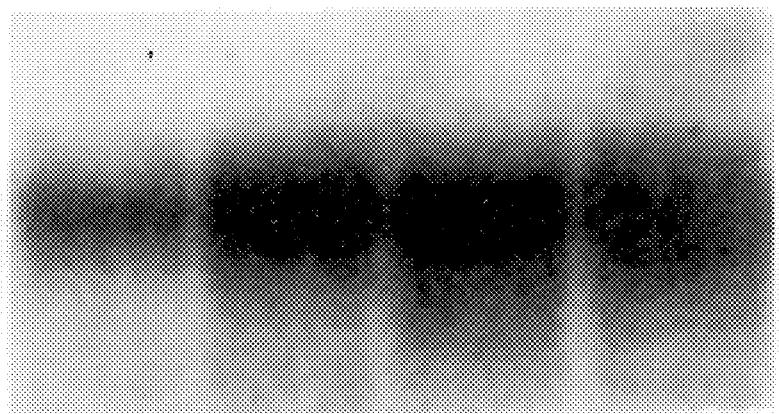
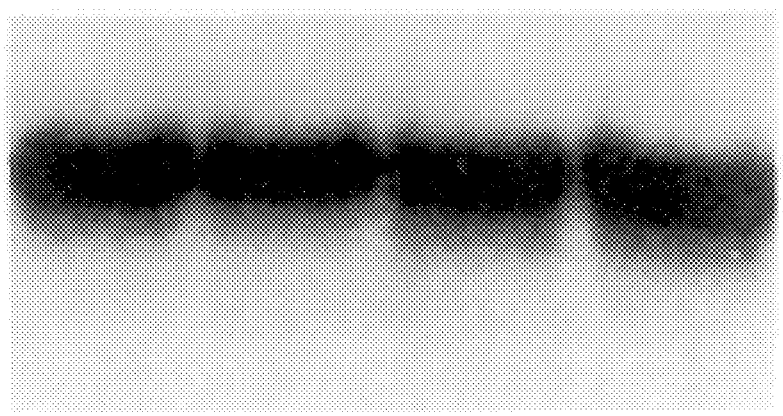
FIG.5

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2905 base pairs
      (B) TYPE: nucleic acid
      (C) STRANDEDNESS: both
      (D) TOPOLOGY: both (ii) MOLECULE TYPE: DNA (genomic)

(ix) FEATURE:
      (A) NAME/KEY: CDS
      (B) LOCATION: 107..2365

(xi) SEQUENCE DESCRIPTION: SEQ ID NO:1:

```
GTGCTCTTTG ACTGAGCACC GAGGGGCAGT TGGCAGCTTC ACCTCAGAGC TGCAGGAAGG         60

AACGGGGCAG TGAAAATCGA ATCGGGTGTG ATCCTAGGCC AAGCTC ATG GCC CAG          115
                                                Met Ala Gln
                                                  1

CAG GGC CAG CAG GGG CAA ATG GCA AGT GGA GAC AGC AAT CTC AAC TTC         163
Gln Gly Gln Gln Gly Gln Met Ala Ser Gly Asp Ser Asn Leu Asn Phe
  5                  10                  15

AGG ATG GTC GCA GAG ATC CAG AAC GTA GAG GGT CAG AAC CTG CAG GAG         211
```

```
Arg Met Val Ala Glu Ile Gln Asn Val Glu Gly Gln Asn Leu Gln Glu
 20                  25                  30                  35

CAG GTT TGC CCT GAG CCC ATT TTC AGG TTC TTC AGA GAA AAC AAG GTG          259
Gln Val Cys Pro Glu Pro Ile Phe Arg Phe Phe Arg Glu Asn Lys Val
                 40                  45                  50

GAG ATT GCA AGT GCA ATA ACA AGG CCA TTT CCT TTC CTT ATG GGC CTC          307
Glu Ile Ala Ser Ala Ile Thr Arg Pro Phe Pro Phe Leu Met Gly Leu
             55                  60                  65

CGA GAC CGC TCC TTC ATC TCC GAG CAG ATG TAT GAA CAT TTT CAA GAA          355
Arg Asp Arg Ser Phe Ile Ser Glu Gln Met Tyr Glu His Phe Gln Glu
         70                  75                  80

GCT TTT AGA AAC CTG GTC CCA GTG ACA AGA GTG ATG TAT TGT GTA CTC          403
Ala Phe Arg Asn Leu Val Pro Val Thr Arg Val Met Tyr Cys Val Leu
     85                  90                  95

AGT GAA CTG GAG AAG ACA TTT GGC TGG TCA CAT CTG GAA GCA TTG TTC          451
Ser Glu Leu Glu Lys Thr Phe Gly Trp Ser His Leu Glu Ala Leu Phe
100                 105                 110                 115

AGC AGG ATT AAC CTG ATG GCC TAT CCT GAT TTA AAC GAG ATT TAC AGA          499
Ser Arg Ile Asn Leu Met Ala Tyr Pro Asp Leu Asn Glu Ile Tyr Arg
                120                 125                 130

AGC TTC CAG AAT GTA TGC TAT GAA CAC TCA CCT CTC CAA ATG AAT AAT          547
Ser Phe Gln Asn Val Cys Tyr Glu His Ser Pro Leu Gln Met Asn Asn
            135                 140                 145

GTA AAC GAT TTA GAA GAT AGA CCC AGA TTA CTA CCA TAT GGT AAA CAA          595
Val Asn Asp Leu Glu Asp Arg Pro Arg Leu Leu Pro Tyr Gly Lys Gln
        150                 155                 160

GAG AAC AGC AAT GCC TGT CAT GAA ATG GAT GAT ATA GCA GTG CCT CAG          643
Glu Asn Ser Asn Ala Cys His Glu Met Asp Asp Ile Ala Val Pro Gln
    165                 170                 175

GAA GCC TTG AGC TCC TCG GCA AGG TGT GAG CCA GGT TTC TCT TCA GAG          691
Glu Ala Leu Ser Ser Ser Ala Arg Cys Glu Pro Gly Phe Ser Ser Glu
180                 185                 190                 195

TCT TGT GAG CAG TTA GCT CTC CCA AAG GCT GGT GGA GGA GAT GCT GAA          739
Ser Cys Glu Gln Leu Ala Leu Pro Lys Ala Gly Gly Gly Asp Ala Glu
                200                 205                 210

GAT GCA CCC AGC CTA CTA CCA GTG TCC TGT AAA CTT GCT ATA CAA ATA          787
Asp Ala Pro Ser Leu Leu Pro Val Ser Cys Lys Leu Ala Ile Gln Ile
            215                 220                 225

GAT GAA GGA GAA TCA GAA GAA ATG CCC AAG TTA CTG CCT TAT GAT ACA          835
Asp Glu Gly Glu Ser Glu Glu Met Pro Lys Leu Leu Pro Tyr Asp Thr
        230                 235                 240

GAA GAG ACC TTT GAT CTA AAA ACT CCC CAA GTC ACT AAT GAA GGA GAA          883
Glu Glu Thr Phe Asp Leu Lys Thr Pro Gln Val Thr Asn Glu Gly Glu
    245                 250                 255

CCA GAG AAG GGG CTC TGT CTA CTA CCA GGT GAA GGA GAA GAG GGC AGT          931
Pro Glu Lys Gly Leu Cys Leu Leu Pro Gly Glu Gly Glu Glu Gly Ser
260                 265                 270                 275

GAT GAC TGT TCG GAA ATG TGT GAT GGA GAA GAG CGC CAG GAA GCC TCT          979
Asp Asp Cys Ser Glu Met Cys Asp Gly Glu Glu Arg Gln Glu Ala Ser
                280                 285                 290

AGC TCC CTA GCA AGA CGT GGG TCA GTG TCT AGT GAA CTA GAA AAT CAC         1027
Ser Ser Leu Ala Arg Arg Gly Ser Val Ser Ser Glu Leu Glu Asn His
            295                 300                 305

CCA ATG AAT GAA GAA GGA GAA TCA GAA GAG CTT GCT TCT AGC CTG CTA         1075
Pro Met Asn Glu Glu Gly Glu Ser Glu Glu Leu Ala Ser Ser Leu Leu
        310                 315                 320

TAT GAT AAT GTA CCA GGA GCG GAG CAA TCA GCA TAT GAA AAT GAG AAG         1123
Tyr Asp Asn Val Pro Gly Ala Glu Gln Ser Ala Tyr Glu Asn Glu Lys
    325                 330                 335
```

```
TGT TCC TGT GTC ATG TGT TTC TCA GAA GAG GTG CCA GGA AGC CCA GAA      1171
Cys Ser Cys Val Met Cys Phe Ser Glu Glu Val Pro Gly Ser Pro Glu
340                 345                 350                 355

GCA AGG ACG GAA AGT GAT CAA GCG TGT GGC ACA ATG GAT ACT GTG GAT      1219
Ala Arg Thr Glu Ser Asp Gln Ala Cys Gly Thr Met Asp Thr Val Asp
                360                 365                 370

ATT GCA AAC AAC TCC ACT TTG GGA AAA CCC AAG AGG AAA AGA AGA AAA      1267
Ile Ala Asn Asn Ser Thr Leu Gly Lys Pro Lys Arg Lys Arg Arg Lys
            375                 380                 385

AAG AGG GGG CAT GGC TGG AGC AGA ATG AGA ATG AGA AGG CAG AAA AAC      1315
Lys Arg Gly His Gly Trp Ser Arg Met Arg Met Arg Arg Gln Lys Asn
        390                 395                 400

AGC CAA CAA AAT GAT AAT AGC AAA GCC GAC GGC CAG GTG GTC TCC AGT      1363
Ser Gln Gln Asn Asp Asn Ser Lys Ala Asp Gly Gln Val Val Ser Ser
    405                 410                 415

GAA AAG AAG GCG AAC GTG AAT CTG AAA GAC CTT TCC AAG ATT AGG GGG      1411
Glu Lys Lys Ala Asn Val Asn Leu Lys Asp Leu Ser Lys Ile Arg Gly
420                 425                 430                 435

AGA AAG AGA GGC AAA CCT GGA ACC CGC TTC ACT CAG AGT GAC AGA GCT      1459
Arg Lys Arg Gly Lys Pro Gly Thr Arg Phe Thr Gln Ser Asp Arg Ala
                440                 445                 450

GCA CAG AAA AGA GTC CGA TCA AGA GCT TCA AGA AAG CAC AAA GAT GAA      1507
Ala Gln Lys Arg Val Arg Ser Arg Ala Ser Arg Lys His Lys Asp Glu
            455                 460                 465

ACT GTG GAT TTT AAG GCT CCT TTG CTT CCA GTG ACC TGT GGT GGG GTG      1555
Thr Val Asp Phe Lys Ala Pro Leu Leu Pro Val Thr Cys Gly Gly Val
        470                 475                 480

AAG GGA ATT TTA CAT AAG AAG AAA TTG CAG CAA GGA ATC TTG GTG AAG      1603
Lys Gly Ile Leu His Lys Lys Lys Leu Gln Gln Gly Ile Leu Val Lys
    485                 490                 495

TGT ATA CAG ACT GAG GAT GGA AAA TGG TTC ACC CCC ACG GAA TTT GAA      1651
Cys Ile Gln Thr Glu Asp Gly Lys Trp Phe Thr Pro Thr Glu Phe Glu
500                 505                 510                 515

ATC AAA GGA GGC CAT GCA AGA TCA AAG AAC TGG AGG CTG AGT GTG CGC      1699
Ile Lys Gly Gly His Ala Arg Ser Lys Asn Trp Arg Leu Ser Val Arg
                520                 525                 530

TGT GGC GGG TGG CCC CTA CGA TGG CTG ATG GAG AAT GGA TTT CTG CCT      1747
Cys Gly Gly Trp Pro Leu Arg Trp Leu Met Glu Asn Gly Phe Leu Pro
            535                 540                 545

GAT CCT CCA AGA ATA CGT TAC AGG AAA AAA AAG AGA ATA CTG AAG TCT      1795
Asp Pro Pro Arg Ile Arg Tyr Arg Lys Lys Lys Arg Ile Leu Lys Ser
        550                 555                 560

CAA AAC AAT AGC TCA GTT GAC CCT TGT ATG AGA AAC CTG GAT GAG TGT      1843
Gln Asn Asn Ser Ser Val Asp Pro Cys Met Arg Asn Leu Asp Glu Cys
    565                 570                 575

GAG GTG TGC CGG GAC GGA GGG GAG CTG TTC TGT TGC GAC ACT TGT TCA      1891
Glu Val Cys Arg Asp Gly Gly Glu Leu Phe Cys Cys Asp Thr Cys Ser
580                 585                 590                 595

AGA GTC TTC CAT GAG GAC TGT CAC ATC CCG CCT GTG GAA GCT GAG AGG      1939
Arg Val Phe His Glu Asp Cys His Ile Pro Pro Val Glu Ala Glu Arg
                600                 605                 610

ACC CCG TGG AAT TGC ATC TTC TGC AGG ATG AAG GAG TCT CCG GGA AGC      1987
Thr Pro Trp Asn Cys Ile Phe Cys Arg Met Lys Glu Ser Pro Gly Ser
            615                 620                 625

CAA CAG TGT TGT CAG GAA TCT GAG GTC CTG GAG AGG CAG ATG TGT CCT      2035
Gln Gln Cys Cys Gln Glu Ser Glu Val Leu Glu Arg Gln Met Cys Pro
        630                 635                 640

GAG GAA CAG TTG AAA TGT GAG TTC CTC CTC TTG AAA GTC TAT TGC TGT      2083
Glu Glu Gln Leu Lys Cys Glu Phe Leu Leu Leu Lys Val Tyr Cys Cys
    645                 650                 655
```

```
TCT GAG AGC TCC TTT TTT GCC AAG ATT CCA TAC TAT TAT TAT ATT AGA          2131
Ser Glu Ser Ser Phe Phe Ala Lys Ile Pro Tyr Tyr Tyr Tyr Ile Arg
660                 665                 670                 675

GAG GCG TGT CAA GGC CTG AAG GAG CCC ATG TGG TTG GAT AAA ATC AAG          2179
Glu Ala Cys Gln Gly Leu Lys Glu Pro Met Trp Leu Asp Lys Ile Lys
                680                 685                 690

AAA AGG CTG AAT GAG CAC GGT TAC CCC CAA GTG GAG GGG TTT GTA CAA          2227
Lys Arg Leu Asn Glu His Gly Tyr Pro Gln Val Glu Gly Phe Val Gln
            695                 700                 705

GAC ATG CGC CTC ATC TTC CAG AAC CAC AGG GCC TCT TAC AAG TAC AAG          2275
Asp Met Arg Leu Ile Phe Gln Asn His Arg Ala Ser Tyr Lys Tyr Lys
        710                 715                 720

GAT TTT GGC CAA ATG GGA TTT AGA CTG GAG GCT GAG TTT GAG AAG AAT          2323
Asp Phe Gly Gln Met Gly Phe Arg Leu Glu Ala Glu Phe Glu Lys Asn
    725                 730                 735

TTC AAG GAA GTG TTT GCT ATT CAG GAA ACA AAT GGG AAC AAT                  2365
Phe Lys Glu Val Phe Ala Ile Gln Glu Thr Asn Gly Asn Asn
740                 745                 750

TGACTGGATT AGTGGATGCT GAAAGCATTC AGCAAATGGC ACCCTAAAAT ATGCCGCTGG        2425

TTTGCCACTG ACTTCAAAAT GAGGTCACTT GGGCACAGCA CATGCAGGGA GGGGCTTTTC        2485

TCTGAGCCTC CTTCATCTGC CCAAAGACAA ATCCTCAAAA GGAAATTCAA TCATCATGAA        2545

TCACAACCCC AAGTATCTCA TCAGCCAGGG AAGAGTAAGT GGGATCACAG GGAAGGATGT        2605

TGGCAGCGAC ACCATCCCAT ACAGGCTCTT ACCTCTTCTC CTGAGGGCTG CTCCAGACAA        2665

CATTTATTAC CCAGAAGACC TTTTGTCTGA AAACCAGCCA AGCTTTATTC AGGACACACT        2725

TCTTGCCTTC ACTTTCCCAC TTCCGTGGCC ACCTCCATGC AGAAGCCCTA AGCCCACATT        2785

CTTTCAATAG CTCACGGTGG TGCATGAGTG TCCATCATCT GACTCTTCTC GGAGTCTCAT        2845

ATTTTGTGGG ACTCCTGTGC AAACATATGT TATTAAAATT TTTTTCCTCC TGTAAAGGAA        2905

(2) INFORMATION FOR SEQ ID NO:2:

(i) SEQUENCE CHARACTERISTICS:
        (A) LENGTH: 753 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Gln Gln Gly Gln Gln Gly Gln Met Ala Ser Gly Asp Ser Asn
 1               5                  10                  15

Leu Asn Phe Arg Met Val Ala Glu Ile Gln Asn Val Glu Gly Gln Asn
                20                  25                  30

Leu Gln Glu Gln Val Cys Pro Glu Pro Ile Phe Arg Phe Arg Glu
            35                  40                  45

Asn Lys Val Glu Ile Ala Ser Ala Ile Thr Arg Pro Phe Pro Phe Leu
    50                  55                  60

Met Gly Leu Arg Asp Arg Ser Phe Ile Ser Glu Gln Met Tyr Glu His
65                  70                  75                  80

Phe Gln Glu Ala Phe Arg Asn Leu Val Pro Val Thr Arg Val Met Tyr
                85                  90                  95

Cys Val Leu Ser Glu Leu Glu Lys Thr Phe Gly Trp Ser His Leu Glu
                100                 105                 110

Ala Leu Phe Ser Arg Ile Asn Leu Met Ala Tyr Pro Asp Leu Asn Glu
            115                 120                 125
```

-continued

```
Ile Tyr Arg Ser Phe Gln Asn Val Cys Tyr Glu His Ser Pro Leu Gln
    130                 135                 140
Met Asn Val Asn Asp Leu Glu Asp Arg Pro Arg Leu Leu Pro Tyr
145                 150                 155                 160
Gly Lys Gln Glu Asn Ser Asn Ala Cys His Glu Met Asp Asp Ile Ala
                    165                 170                 175
Val Pro Gln Glu Ala Leu Ser Ser Ser Ala Arg Cys Glu Pro Gly Phe
                180                 185                 190
Ser Ser Glu Ser Cys Glu Gln Leu Ala Leu Pro Lys Ala Gly Gly Gly
            195                 200                 205
Asp Ala Glu Asp Ala Pro Ser Leu Leu Pro Val Ser Cys Lys Leu Ala
        210                 215                 220
Ile Gln Ile Asp Glu Gly Glu Ser Glu Glu Met Pro Lys Leu Leu Pro
225                 230                 235                 240
Tyr Asp Thr Glu Glu Thr Phe Asp Leu Lys Thr Pro Gln Val Thr Asn
                245                 250                 255
Glu Gly Glu Pro Glu Lys Gly Leu Cys Leu Leu Pro Gly Glu Gly Glu
                260                 265                 270
Glu Gly Ser Asp Asp Cys Ser Glu Met Cys Asp Gly Glu Glu Arg Gln
            275                 280                 285
Glu Ala Ser Ser Ser Leu Ala Arg Arg Gly Ser Val Ser Ser Glu Leu
        290                 295                 300
Glu Asn His Pro Met Asn Glu Glu Gly Glu Ser Glu Glu Leu Ala Ser
305                 310                 315                 320
Ser Leu Leu Tyr Asp Asn Val Pro Gly Ala Glu Gln Ser Ala Tyr Glu
                325                 330                 335
Asn Glu Lys Cys Ser Cys Val Met Cys Phe Ser Glu Glu Val Pro Gly
                340                 345                 350
Ser Pro Glu Ala Arg Thr Glu Ser Asp Gln Ala Cys Gly Thr Met Asp
            355                 360                 365
Thr Val Asp Ile Ala Asn Asn Ser Thr Leu Gly Lys Pro Lys Arg Lys
        370                 375                 380
Arg Arg Lys Lys Arg Gly His Gly Trp Ser Arg Met Arg Met Arg Arg
385                 390                 395                 400
Gln Lys Asn Ser Gln Asn Asp Asn Ser Lys Ala Asp Gly Gln Val
                405                 410                 415
Val Ser Ser Glu Lys Lys Ala Asn Val Asn Leu Lys Asp Leu Ser Lys
                420                 425                 430
Ile Arg Gly Arg Lys Arg Gly Lys Pro Gly Thr Arg Phe Thr Gln Ser
            435                 440                 445
Asp Arg Ala Ala Gln Lys Arg Val Arg Ser Arg Ala Ser Arg Lys His
        450                 455                 460
Lys Asp Glu Thr Val Asp Phe Lys Ala Pro Leu Leu Pro Val Thr Cys
465                 470                 475                 480
Gly Gly Val Lys Gly Ile Leu His Lys Lys Leu Gln Gln Gly Ile
                485                 490                 495
Leu Val Lys Cys Ile Gln Thr Glu Asp Gly Lys Trp Phe Thr Pro Thr
            500                 505                 510
Glu Phe Glu Ile Lys Gly Gly His Ala Arg Ser Lys Asn Trp Arg Leu
        515                 520                 525
Ser Val Arg Cys Gly Gly Trp Pro Leu Arg Trp Leu Met Glu Asn Gly
        530                 535                 540
Phe Leu Pro Asp Pro Pro Arg Ile Arg Tyr Arg Lys Lys Lys Arg Ile
```

-continued

```
545                 550                 555                 560
Leu Lys Ser Gln Asn Asn Ser Val Asp Pro Cys Met Arg Asn Leu
                565                 570                 575
Asp Glu Cys Glu Val Cys Arg Asp Gly Gly Glu Leu Phe Cys Cys Asp
                580                     585                 590
Thr Cys Ser Arg Val Phe His Glu Asp Cys His Ile Pro Pro Val Glu
                595                 600                 605
Ala Glu Arg Thr Pro Trp Asn Cys Ile Phe Cys Arg Met Lys Glu Ser
    610                 615                 620
Pro Gly Ser Gln Gln Cys Gln Glu Ser Glu Val Leu Glu Arg Gln
625                 630                 635                 640
Met Cys Pro Glu Glu Gln Leu Lys Cys Glu Phe Leu Leu Leu Lys Val
                645                 650                 655
Tyr Cys Cys Ser Glu Ser Ser Phe Phe Ala Lys Ile Pro Tyr Tyr Tyr
                660                 665                 670
Tyr Ile Arg Glu Ala Cys Gln Gly Leu Lys Glu Pro Met Trp Leu Asp
                675                 680                 685
Lys Ile Lys Lys Arg Leu Asn Glu His Gly Tyr Pro Gln Val Glu Gly
    690                 695                 700
Phe Val Gln Asp Met Arg Leu Ile Phe Gln Asn His Arg Ala Ser Tyr
705                 710                 715                 720
Lys Tyr Lys Asp Phe Gly Gln Met Gly Phe Arg Leu Glu Ala Glu Phe
                725                 730                 735
Glu Lys Asn Phe Lys Glu Val Phe Ala Ile Gln Glu Thr Asn Gly Asn
                740                 745                 750
Asn
```

(2) INFORMATION FOR SEQ ID NO:3:

(i) SEQUENCE CHARACTERISTICS:
        (A) LENGTH: 129 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Glu Gly Gln Asn Leu Gln Glu Gln Val Cys Pro Glu Pro Ile Phe Arg
1               5                   10                  15
Phe Phe Arg Glu Asn Lys Val Glu Ile Ala Ser Ala Ile Thr Arg Pro
                20                  25                  30
Phe Pro Phe Leu Met Gly Leu Arg Asp Arg Ser Phe Ile Ser Glu Gln
            35                  40                  45
Met Tyr Glu His Phe Gln Glu Ala Phe Arg Asn Leu Val Pro Val Thr
        50                  55                  60
Arg Val Met Tyr Cys Val Leu Ser Glu Leu Glu Lys Thr Phe Gly Trp
65                  70                  75                  80
Ser His Leu Glu Ala Leu Phe Ser Arg Ile Asn Leu Met Ala Tyr Pro
                85                  90                  95
Asp Leu Asn Glu Ile Tyr Arg Ser Phe Gln Asn Val Cys Tyr Glu His
                100                 105                 110
Ser Pro Leu Gln Met Asn Asn Val Asn Asp Leu Glu Asp Arg Pro Arg
            115                 120                 125
Leu
```

(2) INFORMATION FOR SEQ ID NO:4:

(i) SEQUENCE CHARACTERISTICS:
        (A) LENGTH: 129 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Glu Asp Gln Gly Val Asp Asp Arg Leu Leu Tyr Asp Ile Val Phe Lys
 1               5                  10                  15

His Phe Lys Arg Asn Lys Val Glu Ile Ser Asn Ala Ile Lys Lys Thr
             20                  25                  30

Phe Pro Phe Leu Glu Gly Leu Arg Asp Arg Asp Leu Ile Thr Asn Lys
             35                  40                  45

Met Phe Glu Asp Ser Gln Asp Ser Cys Arg Asn Leu Val Pro Val Gln
 50                  55                  60

Arg Val Val Tyr Asn Val Leu Ser Glu Leu Glu Lys Thr Phe Asn Leu
 65                  70                  75                  80

Pro Val Leu Glu Ala Leu Phe Ser Asp Val Asn Met Gln Glu Tyr Pro
             85                  90                  95

Asp Leu Ile His Ile Tyr Lys Gly Phe Glu Asn Val Ile His Asp Lys
             100                 105                 110

Leu Pro Leu Gln Glu Ser Glu Glu Glu Arg Glu Glu Arg Ser Gly
             115                 120                 125

Leu
```

(2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Leu Lys Glu Pro Met Trp Leu Asp Lys Ile Lys Lys Arg Leu Asn Glu
 1               5                  10                  15

His Gly Tyr Pro Gln Val Glu Gly Phe Val Gln Asp Met Arg Leu Ile
             20                  25                  30

Phe Gln Asn
         35
```

(2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Val Lys Glu Pro Met Asp Leu Gly Thr Ile Ala Lys Lys Leu Asn Asp
 1               5                  10                  15

Trp Gln Tyr Gln Thr Met Glu Asp Phe Glu Arg Asp Val Arg Leu Val
             20                  25                  30
```

```
Phe Lys Asn
    35

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:7:

CCTGAGGCAC TGCTATAT                                               18

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:8:

CGGAATTCGA AATGGCCTTG TTATTG                                      26
```

LEUKOCYTE-SPECIFIC PROTEIN AND GENE, AND METHODS OF USE THEREOF

CROSS REFERENCE TO RELATED APPLICATION

This application claims priority to U.S. Provisional Application No. 60/027,347, filed Oct. 2, 1996, the contents of which are incorporated herein by reference.

STATEMENT AS TO RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention is in the fields of molecular and cellular biology and biomedical diagnostics and therapeutics. Specifically, the invention relates to novel nucleic acid molecules, proteins and polypeptide fragments encoded thereby, polyclonal and monoclonal antibodies thereto, and methods of using the nucleic acid molecules, proteins/polypeptides and antibodies in diagnostic, prognostic and therapeutic regimens for the control of autoimmune disorders, viral diseases and cancers.

2. Related Art

The nuclear body (NB, also known as nuclear domain 10, PML oncogenic domain, and Kr body) is a nuclear organelle whose function is unknown (Ascoli, C. A., and Maul, G. G., *J. Cell. Biol.* 112:785–795 (1991); Brasch, K., and Ochs, R. L., *Exp. Cell Res.* 202:211–223 (1992); Dyck, J. A. et al., *Cell* 76:333–343 (1994)). Using immunohistochemical staining, NBs appear as 5 to 30 discrete, punctate, dot-like regions within the nucleus. The NB is distinct from other nuclear domains including those involved in DNA replication and mRNA processing. In addition, components of the NB do not co-localize with kinetochores or centromeres (Brasch, K., and Ochs, R. L., *Exp. Cell Res.* 202:211–223 (1992)). The number of NBs in the cell, and the intensity of antibody staining of these structures, increase in response to stimuli including interferons (IFNs), heat shock and viral infection (Ascoli, C. A., and Maul, G. G., *J. Cell. Biol.* 112:785–795 (1991)).

The NB is a target of autoantibodies in the serum of patients with the autoimmune disease primary biliary cirrhosis (PBC). Approximately 40% of patients with PBC have antibodies directed against this structure (Evans, J., et al., *Arthr. Rheum.* 347:31–736 (1991); Szostecki, C. et al., *Scand. J. Immunol.* 36:555–564 (1992)). Serum from patients with PBC was used to identify and characterize a 100-kDa component of the NB which was designated Sp100 (Speckled, 100 kDa) (Szostecki, C. et al., *J. Immunol.* 145:4338–4347 (1990)). The fusion of Sp100 to the LexA DNA binding domain has been shown to activate gene transcription in *Saccharomyces cerevisiae*, and it has been suggested that Sp100 may participate in activation of transcription of specific regions in the genome (Xie, K. et al., *Mol. Cell. Biol.* 13:6170–6179 (1993)).

A second component of the NB, designated NDP52, was characterized using a murine monoclonal antibody that reacted with the NB (Korioth, F., et al., *J. Cell. Biol.* 130:1–13 (1995)). A cDNA encoding NDP52 was identified and the predicted amino acid sequence contained coiled coil, leucine zipper and zinc finger motifs. One or more of these domains may be involved in interactions between NDP52 and other components of the NB (Korioth, F., et al., *J. Cell. Biol.* 130:1–13 (1995)).

A third component of the NB, PML, was identified by several investigators studying the t(15;17) translocation associated with human acute promyelocytic leukemia (APL) (de Thé, H. et al., *Nature* (London) 347:558–561 (1990); Borrow, J. et al., *Science* 249:1577–1580 (1990); Longo, L. et al., *J. Exp. Med.* 172:1571–1575 (1990); Kakizuka, A. et al., *Cell* 66:663–674 (1991)). In this translocation, the amino terminal portion of PML is fused to retinoic acid receptor α(RARα). PML was found to co-localize with Sp100 in the NB (Weis, K. et al., *Cell* 76:345–356 (1994); Koken, M. H. M. et al., *EMBO* 13:1073–1083 (1994)). Expression of the PML-RARα fusion protein in APL cells appears to disrupt the NB; in these cells, the NB antigens are detected in numerous smaller regions in the nucleus described as "microspeckles." Treatment of APL cells with retinoic acid (RA) results in differentiation of myeloid precursor cells and reformation of NBs (Dyck, J. A. et al., *Cell* 76:333–343 (1994); Weis, K. et al., *Cell* 76:345–356 (1994); Koken, M. H. M. et al., *EMBO* 13:1073–1083 (1994)). In patients with APL, treatment with RA results in differentiation of leukemic cells and temporary disease remission (Warrell, R. P. et al., *N. Eng. J. Med.* 329:177–189 (1993)).

PML, like Sp100 and NDP52, is expressed in a wide variety of human cells and established cell lines. For example, immunoreactive PML is detectable in myeloid precursor cells as well as in erythroblasts and megakaryocytes in the bone marrow (Daniel, M. T. et al., *Blood* 82:1858–1867 (1993)). In addition, PML has been detected in psoriatic skin lesions, hyperplastic breast and colon tissues, and in the endometrial mucosa during the follicular phase of the menstrual cycle (Koken, M. H. M. et al., *Oncogene* 10:1315–1324 (1995)). In recent studies, it was demonstrated that PML, like Sp100, is a target of autoantibodies in patients with PBC (Stemsdorf, T. et al., *Scand. J. Immunol.* 42:257–268 (1995)).

Recently, a lymphoid-restricted homologue of SP100 termed LYSP100 (for "lymphoid-restricted homologue of SP100") was reported (Dent, A. L. et al., *Blood* 88(4):1423–1436 (1996)). Although found in intact cells as microspeckles associated with the NBs of certain lymphoid cell lines, LYSP100 was reported to be morphologically and spatially distinct from PML in these cells, suggesting that it may represent a novel subnuclear domain. LYSP100 mRNA expression was also found to be restricted to lymphoid tissues such as the spleen, thus further distinguishing this gene from SP100 which is more widespread in its expression (Dent, A. L. et al., *Blood* 88(4):1423–1436 (1996)).

With the possible exception of LYSP100 (which has not yet been examined), expression of the previously identified components of the NB is enhanced by treatment with IFNs (Korioth, F., et al., *J. Cell. Biol.* 130:1–13 (1995); Guldner, H. H. et al., *J. Immunol.* 149:4067–4073 (1992); Doucas, V. et al., *Genes & Devel.* 10:196–207 (1996)). It has been suggested that IFN induction of increased expression of Sp100 reflects a role for Sp100 in the "anti-viral state" (Guldner, H. H. et al., *J. Immunol.* 149:4067–4073 (1992)). In support of this notion, it has been demonstrated that IFN-induced expression of PML in Hep2 cells is associated with inhibition of adenovirus replication (Doucas, V. et al., *Genes & Devel.* 10:196–207 (1996)).

The NB is a site of interaction between viral and host proteins. For example, it has been demonstrated that infection of cells with herpes simplex virus-1 (HSV-1) results in disruption of the NB (Maul, G. G. et al., *J. Gen. Virol.* 74:2679–2690 (1993); Maul, G. G., and Everett, R. D., *J. Gen. Virol.* 75:1223–1233 (1994)). Using HSV-1 deletion mutants, disruption of the nuclear body was shown to be a result of the action of the viral protein ICP0. Recent studies have demonstrated that other viral proteins, including the adenovirus E4-ORF3 protein, also interact with this nuclear organelle (Doucas, V. et al., *Genes & Devel.* 10:196–207 (1996); Puvion-Dutilleul, F. et al., *Exp. Cell. Res.* 218:9–16 (1995); Carvalho, T. et al., *J. Cell. Biol.* 131:45–56 (1995)).

BRIEF SUMMARY OF THE INVENTION

The present invention provides isolated nucleic acid molecules comprising a polynucleotide having a nucleotide sequence at least 95% identical to a sequence selected from the group consisting of (a) a nucleotide sequence corresponding to that set forth in SEQ ID NO:1, (b) a nucleotide sequence encoding the Sp140 polypeptide having an amino acid sequence as set forth in SEQ ID NO:2, and (c) a nucleotide sequence complementary to either of the nucleotide sequences in (a) or (b), and a polynucleotide which hybridizes under stringent hybridization conditions to any of the above polynucleotides. The invention also provides isolated nucleic acid molecules having a complete nucleotide sequence set forth in SEQ ID NO:1, and isolated nucleic acid molecules comprising a polynucleotide which encodes the amino acid sequence of an epitope-bearing portion of a Sp140 polypeptide having an amino acid sequence as set forth in SEQ ID NO:2. The invention further provides methods for making a recombinant vector comprising inserting the above-described isolated nucleic acid molecules into a vector, recombinant vectors produced by these methods, methods of making a recombinant host cell comprising introducing the recombinant vectors into a host cell, and recombinant host cells produced by these methods. The invention also provides recombinant methods for producing a Sp140 polypeptide comprising culturing the above-described recombinant host cells under conditions such that said polypeptide is expressed and recovering the Sp140 polypeptide, and recombinant Sp140 polypeptides produced by these methods. In another embodiment, the invention provides isolated Sp140 polypeptides having an amino acid sequence at least 95% identical to a sequence selected from the group consisting of (a) the amino acid sequence set forth in SEQ ID NO:2; (b) the amino acid sequence of the Sp140 polypeptide having the complete amino acid sequence encoded by the above-described isolated nucleic acid molecules; and (c) the amino acid sequence of an epitope-bearing portion of the Sp140 polypeptide having an amino acid sequence corresponding to that set forth in any one of (a) or (b). The invention also encompasses isolated polypeptides comprising an epitope-bearing portion of the Sp140 protein, wherein the epitope-bearing portion is selected from the group consisting of (a) a polypeptide comprising amino acid residues from about 131 to about 391 in SEQ ID NO:2; (b) a polypeptide comprising amino acid residues from about 131 to about 300 in SEQ ID NO:2; (c) a polypeptide comprising amino acid residues from about 131 to about 250 in SEQ ID NO:2; (d) a polypeptide comprising amino acid residues from about 131 to about 200 in SEQ ID NO:2; and (e) a polypeptide comprising amino acid residues from about 131 to about 150 in SEQ ID NO:2. The present invention further provides isolated antibodies that bind specifically to the above-described isolated polypeptides. Antibodies provided herein may be polyclonal or monoclonal, may be affinity purified, may be immobilized onto a solid support, and may be detectably labeled. The invention also provides methods for detecting the presence of an autoimmune disease in an animal, preferably a human, comprising the steps of isolating a serum sample from the animal, incubating the serum with an isolated Sp140 polypeptide described above, and detecting the binding of autoantibodies in the serum sample to the isolated polypeptide. The invention also provides alternative methods for detecting the presence of an autoimmune disease in an animal comprising the steps of isolating serum from the animal, immobilizing components of the serum on a solid support, contacting the immobilized serum components with an isolated polypeptide described above under conditions favoring the formation of a complex between the serum components and isolated polypeptide, contacting the formed complex with an antibody that binds specificially to Sp140, and detecting the binding of the antibody to the complex. Autoimmune diseases that may be diagnosed by the methods of the present invention include primary biliary cirrhosis, rheumatoid arthritis, systemic lupus erythematosis, Sjögren's syndrome, scleroderma and multiple sclerosis. The present invention also provides methods of treating certain diseases in an animal, preferably a human, by gene therapy wherein an isolated polynucleotide as described above is introduced into the cells of the animal. Diseases treatable by these methods include autoimmune diseases (such as primary biliary cirrhosis, rheumatoid arthritis, systemic lupus erythematosis, Sjögren's syndrome, scleroderma and multiple sclerosis), viral diseases (including those caused by herpes simplex virus, cytomegalovirus, human immunodeficiency virus, hepatitis virus, human T-cell leukemia virus-1 (HTLV-1) and adenovirus) and cancers (including leukemias, particularly acute promyelocytic leukemia, cancers of the breast, ovary, prostate, bone, liver, pancreas or spleen, sarcomas and a melanomas. Particularly preferred in the present invention are gene therapy methods wherein the introduction of the isolated polynucleotide into the cells of the animal induces an increase in the expression of Sp140 in the cells.

Other preferred embodiments of the present invention will be apparent to one of ordinary skill in light of the following drawings and description of the invention, and of the claims.

BRIEF DESCRIPTION OF THE DRAWINGS

FIG. 1. Immunoblot of the in vitro translation product of the Sp140 cDNA Antibodies in human serum reacted with the 140-kDa translation product, as well as other reticulocyte lysate proteins (Panel A; "+" lane). In contrast, the 140-kDa band was not detected in a lane containing only reticulocyte lysate proteins (Panel A; "−" lane). Rat antiserum directed against Sp140 (amino acids 131–391) also reacted with the 140-kDa translation product (Panel B; "+" lane) but not with reticulocyte lysate proteins (Panel B; "−" lane).

FIGS. 2A–2C. Panel A: The nucleotide and predicted amino acid sequences of Sp140 (SEQ ID NOs:1 and 2, respectively). The region of similarity between the amino terminal portions of Sp140 and Sp100 is indicated in italics. A presumed nuclear localization sequence is present between amino acids 381–400 (indicated by box). Conserved cysteine/histidine residues in the zinc finger motif are circled. The bromodomain between amino acids 681–715 is underlined. These sequence data are available from GenBank/EMBL/DDBJ under accession number U63420.

Panel B: Comparison between the amino terminal regions of Sp140 (SEQ ID NO:3) and Sp100 (SEQ ID NO:4). Forty-nine percent of the amino acids in this region are identical.

Panel C: Comparison between Sp140 amino acids 681–715 (SEQ ID NO:5) and a bromodomain in *Saccharomyces cerevisiae* protein BDF1 (SEQ ID NO:6). Seventeen of 35 amino acids in this region are identical.

Figure 3:
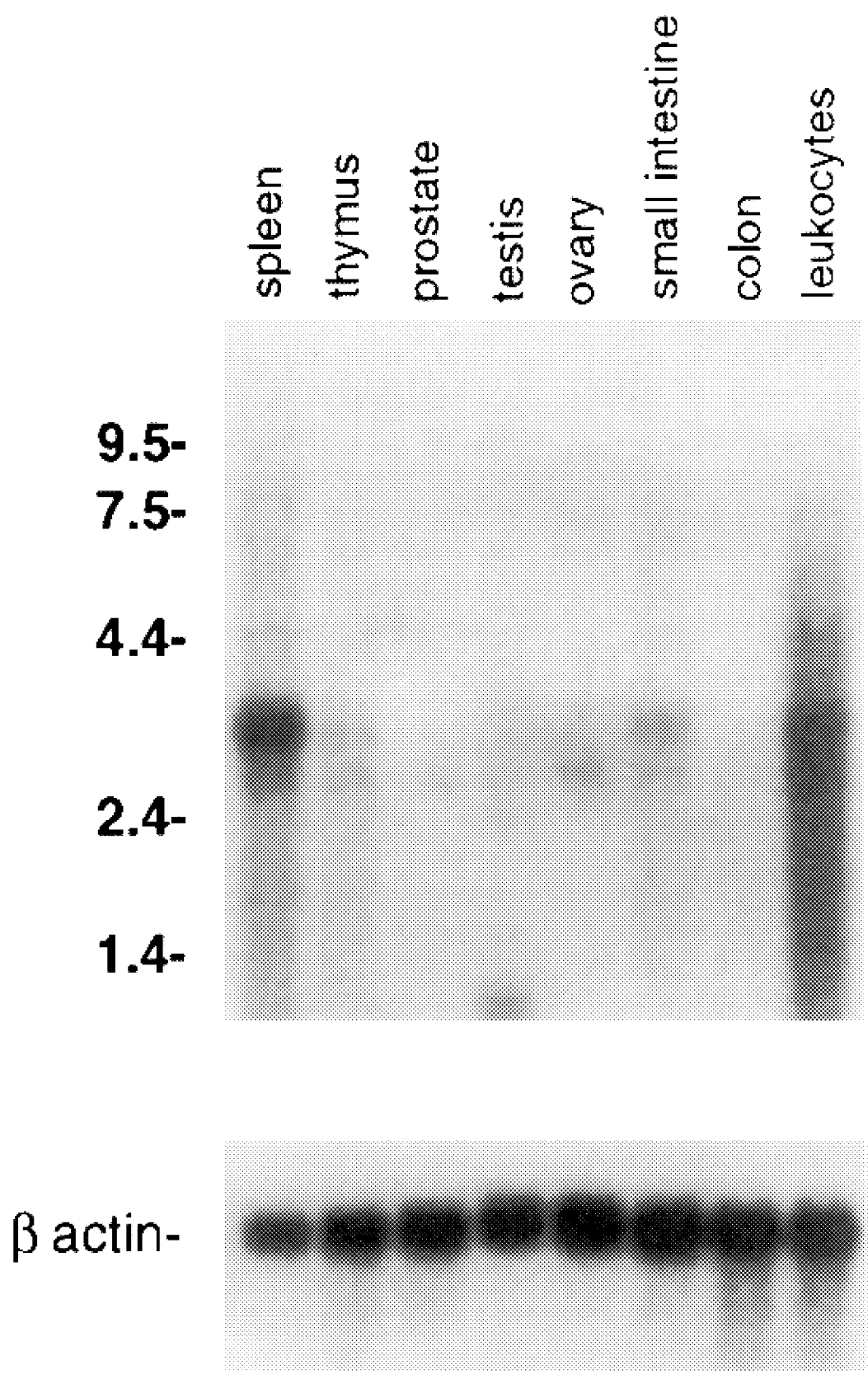

FIG. 3. Identification of Sp140 mRNA in human tissues by RNA blot hybridization. A membrane containing 2.5 µg of poly-(A)+ RNA per lane of human spleen, thymus, prostate, testis, ovary, small intestine, colon, and peripheral blood leukocytes was hybridized with a $^{32}$P-radiolabeled SacI/EcoRI fragment of the Sp140 cDNA. After washing under stringent conditions, the membrane was exposed to autoradiography. High levels of mRNA encoding Sp140 were detected in human spleen and peripheral blood leukocytes. To confirm the presence of RNA in each lane, the membrane was subsequently hybridized with a human β-actin cDNA probe.

Figure 4:
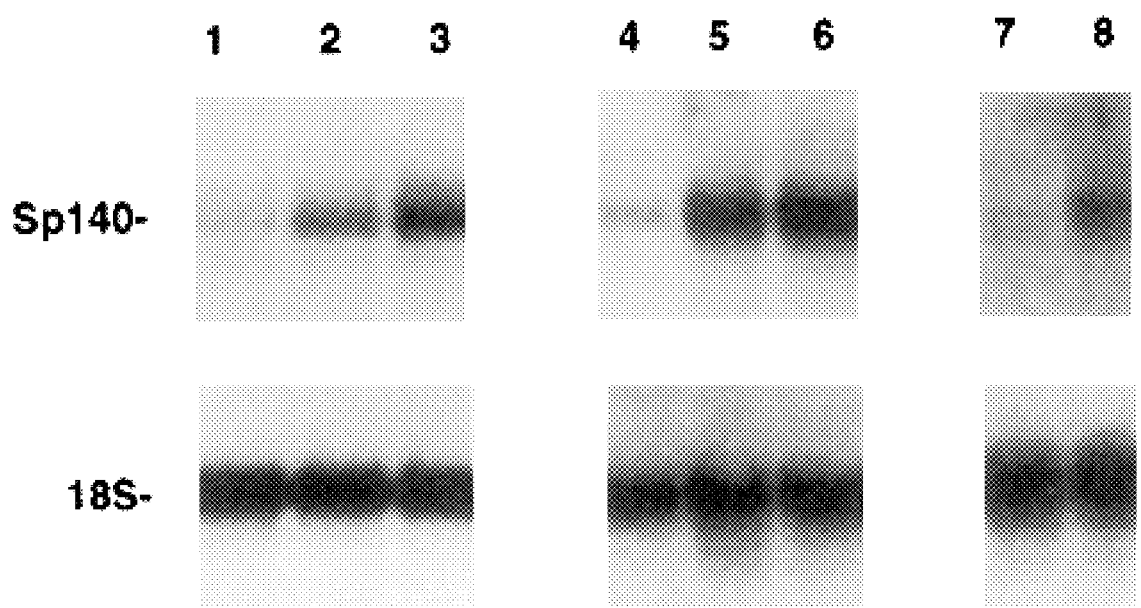

FIG. 4. Expression of Sp140 mRNA in myeloid precursor cell lines. Low levels of Sp140 mRNA were detected in HL60 cells (lanes 1 and 4). Treatment of HL60 cells with PMA (lane 2) or DMSO (lane 5) markedly increased Sp140 gene expression. The level of Sp140 mRNA was further increased by combinations of PMA and IFNγ (lane 3) or DMSO and IFNγ (lane 6). Low levels of Sp140 mRNA were detected in NB4 cells (lane 7). After five days of incubation with RA, the level of Sp140 mRNA was markedly increased (lane 8). To confirm comparable loading of RNA in each lane, membranes were hybridized with a 10-fold molar excess of $^3$P-radiolabeled oligonucleotide complimentary to 18S RNA.

FIG. 5. Effect of interferon gamma (IFNγ) treatment on the level of Sp140 mRNA in HL60 cells. Low levels of Sp140 mRNA were detected in untreated HL60 cells (lane 1). Expression of Sp140 mRNA was enhanced 1, 2 and 4 days after addition of IFNγ (lanes 2, 3 and 4). To confirm comparable loading of RNA in each lane, membranes were hybridized with a 10-fold molar excess of $^{32}$P-radiolabeled oligonucleotide complimentary to 18S RNA.

Figure 6:
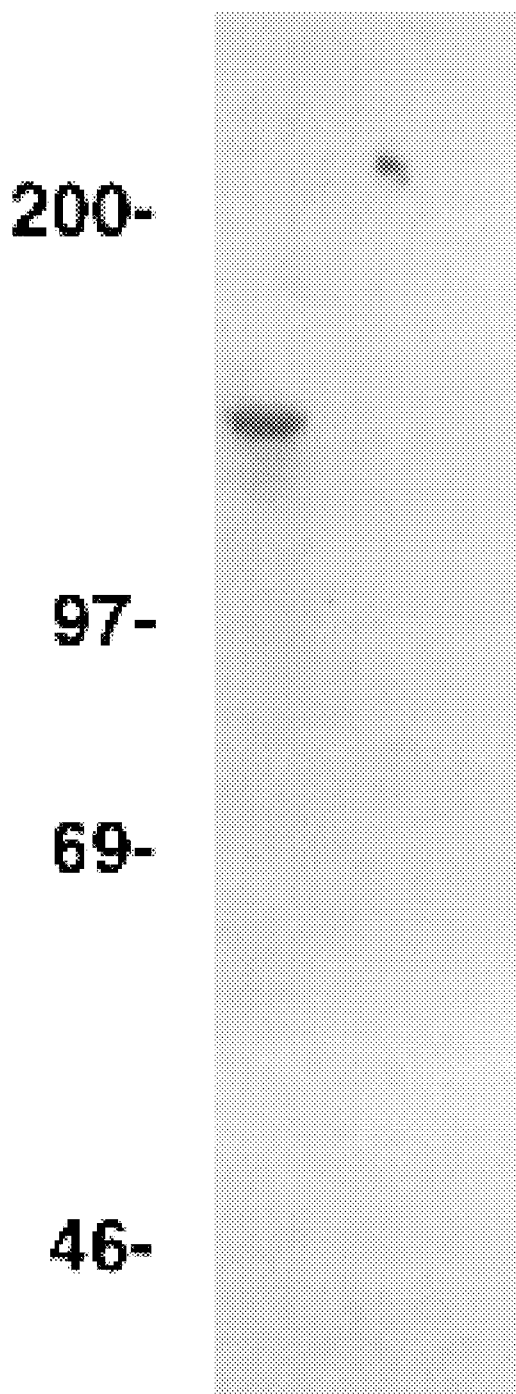
Figure 7A:
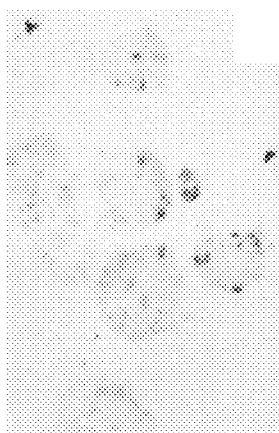
Figure 7B:
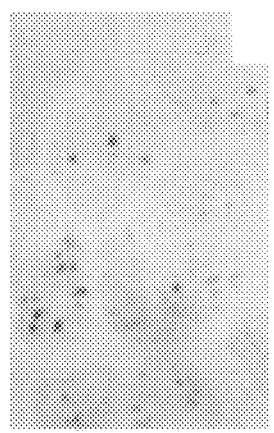
Figure 7C:
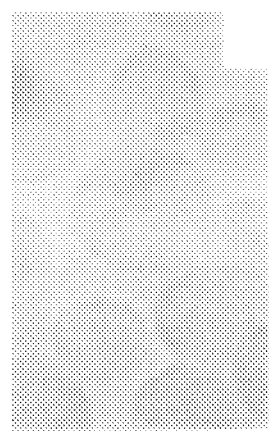
Figure 7D:
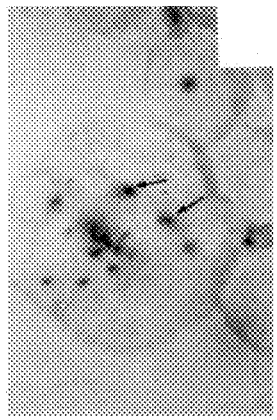
Figure 7E:
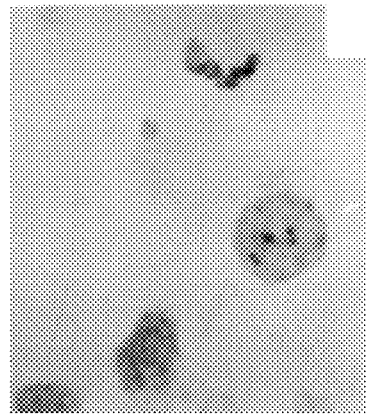
Figure 7F:
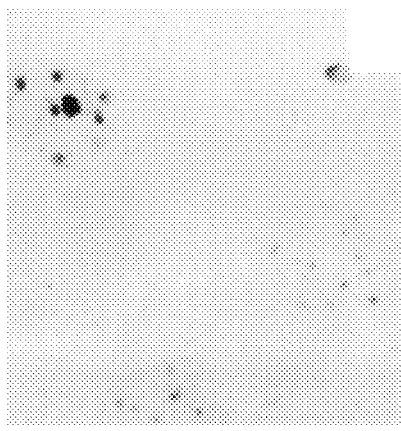
Figure 7G:
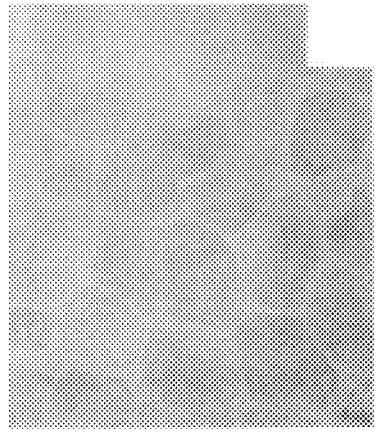

FIG. 6. Immunoblot of proteins isolated from DMSO-treated HL60 cells. Serum from a rat immunized with a fusion protein containing GST-Sp140 (131–391) reacted with a 140-kDa protein in DMSO-treated HL60 cells (lane 1). In contrast, normal rat serum did not react with this protein (data not shown). Rat antiserum pre-incubated with recombinant protein did not react with Sp140 (lane 2).

FIG. 7. Immunohistochemical localization of Sp140 and PML in HL60 cells treated with DMSO and NB4 cells treated with retinoic acid. Affinity-purified rat anti-Sp140 antibodies reacted with dot-like regions in DMSO-treated HL60 cells (panel A). The same staining pattern was seen using mouse monoclonal antibodies directed against PML (panel B). Pre-treatment of rat anti-Sp140 antibodies with recombinant protein blocked the NB staining pattern (panel C). Two color immunohistochemical staining revealed co-localization of Sp140 and PML in the NBs of individual cells (panel D; note the halo of blue surrounding brown-staining NBs, as indicated by arrows). In panels A and C, anti-Sp140 antibodies were revealed with TruBlue peroxidase substrate, resulting, in a blue precipitate. In panels B and D, mouse monoclonal anti-PML antibodies were detected using the DAB substrate, resulting in a brown precipitate. In co-localization studies, Sp140 immunoreactivity was detected using alkaline phosphatase-conjugated reagents and PhThalo Blue. The cells in panels A, C, and D were counterstained lightly with hematoxylin to provide a pale blue contrast, while cells in panel B were counterstained with neutral red dye. Rat anti-Sp140 antiserum reacted with NBs in RA-treated NB4 cells (panel E; DAB brown chromogen). Although the NB staining pattern was most evident in the indicated nucleus (arrow), faint staining of NBs was present in all cells in this field. Mouse monoclonal antibodies directed against PML also reacted with NBs in RA-treated NB4 cells (panel F; TruBlue peroxidase chromogen). Rat antiserum did not react with untreated NB4 cells (panel G).

DETAILED DESCRIPTION OF THE INVENTION

Definitions

In the description that follows, a number of terms and abbreviations conventionally used in the field of molecular and cell biology, and specific to the present invention, are utilized extensively. In order to provide a clear and consistent understanding of the specification and claims, and the scope to be given such terms, the following definitions are provided.

The abbreviation "APL" is used to represent acute promyelocytic leukemia. The term "5'RACE" is used to mean rapid amplification of cDNA 5' ends. "GST" is used herein to represent glutathione-S-transferase. The abbreviation "IFN" is used to represent interferon; thus, "IFNγ" represents interferon gamma. "NB" is used as the abbreviation for nuclear body. "ORF" as used herein is meant to represent open reading frame. "PBC" is used to mean primary biliary cirrhosis. "RA" is used to represent all-trans retinoic acid. Other terms and abbreviations as used herein are standard in the fields to which this invention pertains, and will be understood by one of ordinary skill in the art.

The present invention provides isolated nucleic acid molecules comprising a polynucleotide having the nucleotide sequence shown in FIG. 2A (SEQ ID NO:1). The invention further provides isolated nucleic acid molecules comprising a polynucleotide encoding a Sp140 polypeptide having the amino acid sequence shown in FIG. 2A (SEQ ID NO:2), which was determined by sequencing a cloned cDNA. As is shown in FIG. 2B, the amino terminal portion of the Sp140 protein of the present invention (SEQ ID NO:3) shares about 49% sequence identity with that of Sp100 (SEQ ID NO:4). The nucleotide sequence shown in FIG. 2A (SEQ ID NO:1) was obtained by sequencing a cDNA clone as described below in Example 1. The sequence data are available from GenBank/EMBL/DDBJ under accession number U63420.

Nucleic Acid Molecules

Unless otherwise indicated, all nucleotide sequences determined by sequencing a DNA molecule herein were determined by dideoxy sequencing (Sanger, F., *Science* 214:1205–1210 (1981)), and all amino acid sequences of polypeptides encoded by DNA molecules determined herein were predicted by translation of a DNA sequence determined as above. Therefore, as is known in the art for any DNA sequence determined by this approach, any nucleotide sequence determined herein may contain some errors. Nucleotide sequences determined by these methods are typically at least about 90% identical, more typically at least about 95% to at least about 99.9% identical to the actual nucleotide sequence of the native DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 2A, a nucleic acid molecule of the present invention encoding a Sp140 polypeptide may be obtained using standard cloning and screening procedures, such as those for cloning cDNAs using mRNA as starting material. Illustrative of the invention, the nucleic acid molecule described in FIG. 2A (SEQ ID NO:1) was discovered in a cDNA library derived from HepG2 human hepatocellular carcinoma cells. The gene was also identified in cDNA libraries derived from human umbilical vein endothelial cells (HUVEC) and human placenta. The determined nucleotide sequence of the Sp140 cDNA of FIG. 2A (SEQ ID NO:1) is approximately 2,905 bp in length, contains an open reading frame from bp 107 to 2,365 encoding a protein of 753 amino acid residues (SEQ ID NO:2), with an initiation codon at positions 107–110 of the nucleotide sequence in FIG. 2A (SEQ ID NO:1) preceded by an in-frame stop codon. The deduced molecular weight of the predicted Sp140 polypeptide (SEQ ID NO:2) is about 140 kDa. The amino acid sequence of the predicted Sp140 polypeptide is shown in FIG. 2A (SEQ ID NO:2) from amino acid residue 1 to residue 753. As shown in FIG. 2B, the amino terminal portion of Sp140 (amino acid residues 29–157; SEQ ID NO:3) is about 49% identical to that of the NB-associated protein Sp100 (residues 40–168; SEQ ID NO:4).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 107–110 of the nucleotide sequence shown in FIG. 2A (SEQ ID NO:1); DNA molecules comprising the coding sequence for the mature Sp140 protein shown in FIG. 2A (SEQ ID NO:2); and DNA molecules which comprise a sequence substantially different from those described above but which, due to the degeneracy of the genetic code, still encode the Sp140 protein. Since the genetic code is well known in the art, one skilled in the art can make the degenerate variants described above using routine techniques without undue experimentation.

The present invention is further directed to fragments of the isolated nucleic acid molecules described herein. By a fragment of an isolated nucleic acid molecule having the nucleotide sequence of the nucleotide sequence shown in FIG. 2A (SEQ ID NO:1) is intended fragments at least about 15 nucleotides (nt), more preferably at least about 20 nt, still more preferably at least about 30 nt, and even more preferably, at least about 40 nt in length which are useful as diagnostic probes and primers as discussed herein. Of course, larger fragments 50–2000 nt in length are also useful according to the present invention as are fragments corresponding to most, if not all, of the nucleotide sequence shown in FIG. 2A (SEQ ID NO:1). By a fragment at least 20 nt in length, for example, is intended fragments which include 20 or more contiguous bases from the nucleotide sequence as shown in FIG. 1 (SEQ ID NO:1). Since the nucleotide sequence shown in FIG. 2A (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the Sp140 protein. In particular, such nucleic acid fragments of the present invention include nucleic acid molecules encoding: a polypeptide comprising amino acid residues from about 131 to about 391 in FIG. 2A (SEQ ID NO:2); a polypeptide comprising amino acid residues from about 131 to about 300 in FIG. 2A (SEQ ID NO:2); a polypeptide comprising amino acid residues from about 131 to about 250 in FIG. 2A (SEQ ID NO:2); a polypeptide comprising amino acid residues from about 131 to about 200 in FIG. 2A (SEQ ID NO:2); and a polypeptide comprising amino acid residues from about 131 to about 150 in FIG. 2A (SEQ ID NO:2). The inventors have determined that the above polypeptide fragments are antigenic regions of the Sp140 protein. Methods for determining other such epitope-bearing portions of the Sp140 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, a nucleic acid molecule having a nucleotide sequence as set forth in FIG. 2A (SEQ ID NO:1). By "stringent hybridization conditions" is intended overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides, and more preferably at least about 20 nt, still more preferably at least about 30 nt, and even more preferably about 30–70 nt of the reference polynucleotide. These hybridizing polynucleotides are useful as diagnostic probes and primers as discussed above and in more detail below.

Of course, polynucleotides hybridizing to a larger portion of the reference polynucleotide (e.g., the nucleic acid molecule having a nucleotide sequence set forth in FIG. 2A (SEQ ID NO:1)), for instance, a portion 50–1000 nt in length, or even to the entire length of the reference polynucleotide, are also useful as probes according to the present invention, as are polynucleotides corresponding to most, if not all, of the nucleotide sequence of the nucleotide sequence as shown in FIG. 2A (SEQ ID NO:1). By a portion of a polynucleotide of "at least 20 nt in length," for example, is intended 20 or more contiguous nucleotides from the nucleotide sequence of the reference polynucleotide (e.g., the nucleotide sequence as shown in FIG. 2A (SEQ ID NO:1)). As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a determined nucleotide sequence encoding Sp140 is provided in FIG. 2A (SEQ ID NO:1), generating polynucleotides which hybridize to a portion of the Sp140 cDNA molecule would be routine to the skilled artisan. For example, restriction endonuclease cleavage or shearing by sonication of the Sp140 cDNA clone could easily be used to generate DNA portions of various sizes which are polynucleotides that hybridize to a portion of the Sp140 cDNA molecule. Alternatively, the hybridizing polynucleotides of the present invention could be generated synthetically according to known techniques.

As indicated, nucleic acid molecules of the present invention which encode a Sp140 polypeptide may include, but are not limited to those encoding the amino acid sequence of the mature polypeptide, by itself; the coding sequence for the mature polypeptide and additional sequences, such as those encoding a leader or secretory sequence, such as a pre-, pro- or prepro-protein sequence; the coding sequence of the mature Sp140 polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example; ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the Sp140 polypeptide fused to glutathione S-transferase (GST) at the N- or C-terminus.

The present invention further relates to variants of the nucleic acid molecules of the present invention, which encode portions, analogs or derivatives of the Sp140 protein. Variants may occur naturally, such as a natural allelic variant. By an "allelic variant" is intended one of several alternate forms of a gene occupying a given locus on a chromosome of an organism (see *Genes II*, Lewin, B., ed., John Wiley & Sons, New York (1985)). Non-naturally occurring variants may be produced using mutagenesis techniques that are well-known in the art.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Sp140 protein or portions thereof. Also especially preferred in this regard are conservative substitutions. Most highly preferred are nucleic acid molecules encoding the mature protein having the amino acid sequence shown in FIG. 1 (SEQ ID NO:2).

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence corresponding to that set forth in FIG. 2A (SEQ ID NO:1); (b) a nucleotide sequence encoding the Sp140 polypeptide having an amino acid sequence as set forth in FIG. 2A (SEQ ID NO:2); or (c) a nucleotide sequence complementary to either of the nucleotide sequences in (a) or (b).

By a polynucleotide having a nucleotide sequence at least, for example, 95% "identical" to a reference nucleotide sequence encoding a Sp140 polypeptide is intended that the nucleotide sequence of the polynucleotide is identical to the reference sequence except that the polynucleotide sequence may include up to five point mutations per each 100 nucleotides of the reference nucleotide sequence encoding the Sp140 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 2A (SEQ ID NO:1) can be determined conventionally using known computer programs such as the BESTFIT program (Wisconsin Sequence Analysis Package, Version 8 for Unix, Genetics Computer Group, University Research Park, 575 Science Drive, Madison, Wis. 53711. BESTFIT uses the local homology algorithm of Smith and Waterman, *Adv. Appl. Math.* 2: 482–489 (1981), to find the best segment of homology between two sequences. When using BESTFIT or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 2A (SEQ ID NO:1), irrespective of whether they encode a polypeptide having the activity of Sp140. This is because even where a particular nucleic acid molecule does not encode a polypeptide having Sp140 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Sp140 activity include, inter alia, (1) isolating the Sp140 gene or allelic variants thereof in a cDNA library; (2) in situ hybridization (e.g., "FISH") to metaphase chromosomal spreads to provide precise chromosomal location of the Sp140 gene, as described elsewhere (Verma et al., *Human Chromosomes: A Manual of Basic Techniques,* Pergamon Press, New York (1988)); and (3) northern blot analysis for detecting Sp140 mRNA expression in specific tissues.

Preferred, however, are nucleic acid molecules having sequences at least 90%, 95%, 96%, 97%, 98% or 99% identical to the nucleic acid sequence shown in FIG. 2A (SEQ ID NO:1) which do, in fact, encode a polypeptide having Sp140 protein activity. By "a polypeptide having Sp140 activity" is intended polypeptides exhibiting activity similar, but not necessarily identical, to an activity of the Sp140 protein of the invention, as measured in a particular biological assay.

Although the degree of activity need not be identical to that of the Sp140 protein, preferably, "a polypeptide having Sp140 protein activity" will exhibit substantially similar activity as compared to the Sp140 protein (i.e., the candidate polypeptide will exhibit greater activity or not more than about twenty-fold less and, preferably, not more than about ten-fold less activity relative to the reference Sp140 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 2A (SEQ ID NO:1) will encode a polypeptide "having Sp140 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Sp140 protein activity. This is because the skilled artisan is fully aware of amino acid substitutions that are either less likely or not likely to significantly effect protein function (e.g., replacing one aliphatic amino acid with a second aliphatic amino acid). Guidance concerning how to make phenotypically silent amino acid substitutions is provided in Bowie, J. U., et al., *Science* 247:1306–1310 (1990) and in the references cited therein.

Vectors and Host Cells

The present invention also relates to vectors which comprise the isolated DNA molecules of the present invention, host cells which are genetically engineered with the recombinant vectors, and the production of Sp140 polypeptides or fragments thereof by recombinant techniques.

Recombinant constructs may be introduced into host cells using well known techniques such as infection, transduction, transfection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papovaviruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli,* Streptomyces and *Salmonella typhimurium* cells; fungal cells, such as yeast cells, including Saccharomyces spp.; insect cells such as Drosophila S2 and Spodoptera Sf9 or Sf21 cells; mammalian cells such as CHO, COS, VERO and Bowes melanoma cells; and plant cells. Appropriate culture mediums and conditions for the above-described host cells are well-known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; and pGEX, ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10–300 bp that act to increase transcriptional activity of a promoter in a given host cell-type. Examples of enhancers include the SV40 enhancer, which is located on the late side of the replication origin at bp 100–270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from glutathione S-transferase (GST). For example, the plasmid encoding a portion, or all, of the Sp140 polypeptide depicted in FIG. 2A (SEQ ID NO:2) may be ligated into a GST expression vector such as pGEX (available from Pharmacia). This plasmid may then be used to transform host cells, and expression of the GST-Sp140 fusion protein may be induced by treatment of the transformed host cells with IPTG. The fusion protein comprising the Sp140 polypeptide or fragment thereof can then be purified by affinity chromatography selective for GST, as described (Smith, D. B, and Johnson, K. S., *Gene* 67:31–40 (1988)).

The Sp140 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Sp140 Polypeptides and Fragments

The invention further provides an isolated Sp140 polypeptide having the amino acid sequence encoded by the isolated nucleic acid molecule depicted in FIG. 2A (SEQ ID NO:1), the amino acid sequence in FIG. 2A (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the Sp140 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the Sp140 polypeptide which show substantial Sp140 polypeptide activity or which include regions of Sp140 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. As indicated in detail above, further guidance concerning which amino acid changes are likely to be phenotypically silent (i.e., are not likely to have a significant deleterious effect on a function) can be found in Bowie, J. U., et al., *Science* 247:1306–1310 (1990).

Thus, the fragment, derivative or analog of the polypeptide of FIG. 2A (SEQ ID NO:2), or that encoded by the isolated nucleic acid molecule depicted in FIG. 2A (SEQ ID NO:1), may be (a) one in which one or more of the amino acid residues are substituted with a conserved or non-conserved amino acid residue (preferably a conserved amino acid residue) and such substituted amino acid residue may or may not be one encoded by the genetic code; (b) one in which one or more of the amino acid residues includes a substituent group; (c) one in which the mature polypeptide is fused with another compound, such as a compound to increase the half-life of the polypeptide (for example, polyethylene glycol); or (d) one in which the additional amino acids are fused to the mature polypeptide, such as a GST fusion region peptide or leader or secretory sequence or a sequence which is employed for purification of the mature polypeptide or a proprotein sequence. Such fragments, derivatives and analogs are deemed to be within the scope of those skilled in the art from the teachings herein.

The polypeptides of the present invention are preferably provided in an isolated form, and preferably are substantially purified. A recombinantly produced version of the Sp140 polypeptide can be substantially purified by the one-step method described in Smith and Johnson, *Gene* 67:31–40 (1988).

The polypeptides of the present invention include the polypeptide encoded by the nucleic acid molecule having a nucleotide sequence set forth in FIG. 2A (SEQ ID NO:1) including a leader, the polypeptide encoded by the nucleic acid molecule having a nucleotide sequence set forth in FIG. 2A (SEQ ID NO:1) minus a leader (i.e., the mature polypeptide), the polypeptide of FIG. 2A (SEQ ID NO:2) including the leader, the polypeptide of FIG. 2A (SEQ ID NO:2) minus the leader (i.e., the mature polypeptide), as well as polypeptides which have at least 90% identity, more preferably at least 95% similarity, and still more preferably at least 96%, 97%, 98% or 99% identity to those described above. Further polypeptides of the present invention include polypeptides at least 80% identical, more preferably at least 90% or 95% identical, still more preferably at least 96%, 97%, 98% or 99% identical to the polypeptide encoded by the nucleic acid molecule depicted in FIG. 2A (SEQ ID NO:1) or to the polypeptide of FIG. 2A (SEQ ID NO:2), and also include portions of such polypeptides with at least 30 amino acids and more preferably at least 50 amino acids.

By "% identity" for two polypeptides is intended a identity score produced by comparing the amino acid sequences of the two polypeptides manually, or using, for example, the BESTFIT program as described above.

By a polypeptide having an amino acid sequence at least, for example, 95% "identical" to a reference amino acid sequence of a Sp140 polypeptide is intended that the amino acid sequence of the polypeptide is identical to the reference sequence except that the polypeptide sequence may include up to five amino acid alterations per each 100 amino acids of the reference amino acid of the Sp140 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 2A (SEQ ID NO:2) or to the amino acid sequence encoded by the nucleic acid molecule depicted in FIG. 2A (SEQ ID NO:1), can be determined conventionally using known computer programs such BESTFIT as described above. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As described in detail below, the polypeptides of the present invention can also be used to raise polyclonal and monoclonal antibodies, which are useful in assays for detecting Sp140 protein expression or in methods of diagnosing certain autoimmune, viral and neoplastic diseases, as described below.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., et al., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective.

Antigenic epitope-bearing peptides and polypeptides of the invention are therefore useful to raise antibodies, including polyclonal and monoclonal antibodies mad as described below, that bind specifically to a polypeptide of the invention. Thus, a high proportion of hybridomas obtained by fusion of spleen cells from donors immunized with an antigen epitope-bearing peptide generally secrete antibody reactive with the native protein (Sutcliffe et al., supra, at 663). The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767–778 (1984). The anti-peptide antibodies of the invention also are useful for purification of the mimicked protein, for instance, by adsorption chromatography using methods well-known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate Sp140-specific antibodies include: a polypeptide comprising amino acid residues from about 131 to about 391 in FIG. 2A (SEQ ID NO:2); a polypeptide comprising amino acid residues from about 131 to about 300 in FIG. 2A (SEQ ID NO:2); a polypeptide comprising amino acid residues from about 131 to about 250 in FIG. 2A (SEQ ID NO:2); a polypeptide comprising amino acid residues from about 131 to about 200 in FIG. 2A (SEQ ID NO:2); and a polypeptide comprising amino acid residues from about 131 to about 150 in FIG. 2A (SEQ ID NO:2). As indicated above, the inventors have determined that the above polypeptide fragments are antigenic regions of the Sp140 protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis such as the "Simultaneous Multiple Peptide Synthesis (SMPS)" process (Houghten, R. A., Proc. Natl. Acad. Sci. USA 82:5131–5135 (1985); U.S. Pat. No. 4,631,211).

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, Sp140 polypeptides of the present invention and epitope-bearing fragments thereof may be immobilized onto a solid support, by techniques that are well-known and routine in the art. By "solid support" is intended any solid support to which a peptide can be immobilized. Such solid supports include, but are not limited to nitrocellulose, diazocellulose, glass, polystyrene, polyvinylchloride, polypropylene, polyethylene, dextran, Sepharose, agar, starch, nylon, beads and microtitre plates. Preferred are beads made of glass, latex or a magnetic material. Linkage of the peptide of the invention to a solid support can be accomplished by attaching one or both ends of the peptide to the support. Attachment may also be made at one or more internal sites in the peptide. Multiple attachments (both internal and at the ends of the peptide) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the peptide can be used such as GST (Smith, D. B., and Johnson, K. S., Gene 67:31 (1988)), polyhistidines (Hochuli, E., et al., J. Chromatog. 411:77 (1987)), or biotin. Such affinity tags may be used for the reversible attachment of the peptide to the support. Such immobilized polypeptides or fragments will also be useful, for example, in diagnostic assays determining the presence of antibodies directed against Sp140 in the serum of patients suffering from an autoimmmune, viral or neoplastic disease, as described below.

As one of skill in the art will also appreciate, Sp140 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP 0 394,827; Traunecker et al., *Nature* 331:84–86 (1988)). Fusion proteins that have a disulfide-linked dimeric structure due to the IgG part can also be more efficient in binding and neutralizing other molecules than the monomeric Sp140 protein or protein fragment alone (Fountoulakis et al., *J. Biochem.* 270:3958–3964 (1995)).

Anti-Sp140 Antibodies

Epitope-bearing peptides and polypeptides of the invention are used to induce antibodies according to methods well known in the art, as generally described below (see, e.g., Sutcliffe, et al., supra; Wilson, et al., supra; and Bittle, F. J., et al., *J. Gen. Virol.* 66:2347–2354 (1985)). Animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Sp140 protein-specific antibodies can be raised against the intact Sp140 protein or an antigenic polypeptide fragment thereof, which may presented together with a carrier protein, such as an albumin, to an animal system (such as rabbit, rat or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to [protein name] protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the Sp140 protein or an antigenic fragment thereof can be administered to an animal in order to induce the production of sera containing polyclonal antibodies, according to routine immunological methods. In a preferred method, a preparation of Sp140 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Sp140 protein-binding fragments thereof). Such monoclonal antibodies can be prepared using hybridoma technology Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N.Y., pp. 563–681 (1981)). In general, such procedures involve immunizing an animal (preferably a mouse) with a Sp140 protein antigen or with a Sp140 protein-expressing cell. Suitable cells can be recognized by their capacity to bind anti-Sp140 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterol.* 80:225–232 (1981)). The hybridoma cells obtained through such a selection are then assayed to identify clones which secrete antibodies capable of binding the Sp140 protein antigen.

Alternatively, additional antibodies capable of binding to the Sp140 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Sp140 protein-specific antibodies are used to immunize an animal, preferably a mouse. The splenocytes of such an animal are then used to produce hybridoma cells, and the hybridoma cells are screened to identify clones which produce an antibody whose ability to bind to the Sp140 protein-specific antibody can be blocked by the Sp140 protein antigen. Such antibodies comprise anti-idiotypic antibodies to the Sp140 protein-specific antibody and can be used to immunize an animal to induce formation of further Sp140 protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, Sp140 protein-binding antibody fragments can be produced through the application of recombinant DNA technology or through synthetic chemistry.

Where in vivo imaging is used to detect enhanced levels of Sp140 protein for disease diagnosis in humans (see below), it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi et al., *BioTechniques* 4:214 (1986); U.S. Pat. No. 4,816,567; EP 0 171 496; EP 0 173 494; WO 86/01533; WO 87/02671; Boulianne et al., *Nature* 312:643 (1984); Neuberger et al., *Nature* 314:268 (1985)).

For use, the Sp140 protein-specific antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J. Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31(1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

It will be appreciated by one of ordinary skill that the Sp140 protein-specific antibodies described herein may alternatively be coupled to a solid support, to facilitate, for example, chromatographic and other immunological procedures using such solid phase-immobilized antibodies. By "solid support" is intended any solid support to which an antibody can be immobilized. Such solid supports include, but are not limited to nitrocellulose, diazocellulose, glass, polystyrene, polyvinylchloride, polypropylene, polyethylene, dextran, Sepharose, agar, starch, nylon, beads and microtitre plates. Preferred are beads made of glass, latex or a magnetic material. Linkage of an Sp140 protein-specific antibody of the invention to a solid support can be accomplished by attaching one or both ends of the antibody to the support. Attachment may also be made at one or more internal sites in the antibody. Multiple attachments (both internal and at the ends of the antibody) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the peptide can be used such as GST (Smith, D. B., and Johnson, K. S., *Gene* 67:31 (1988)), polyhistidines (Hochuli, E., et al., *J. Chromatog.* 411:77 (1987)), or biotin. Alternatively, attachment can be accomplished using a ligand which binds the Fc region of the Sp140 protein-binding antibodies, e.g., protein A or protein G. Such affinity tags may be used for the reversible attachment of the antibodies to the support.

Disease Diagnosis and Prognosis

Autoimmune diseases

It is believed that mammals with certain autoimmune diseases express significantly enhanced levels of circulating antibodies directed against Sp140 protein when compared to a corresponding "standard" mammal, i.e., a mammal of the same species not having the autoimmune disease. Thus, the invention provides a diagnostic method useful in autoimmune disease diagnosis, which involves assaying the level of circulating anti-Sp140 antibodies in mammalian cells or body fluid and comparing these antibody levels with a standard anti-Sp140 antibody level, whereby a change (either an increase or a decrease) in the level of circulating anti-Sp140 antibodies over the standard is indicative of certain autoimmune diseases.

Where a diagnosis of an autoimmune disease has already been made according to conventional methods, the present invention is useful as a prognostic indicator, whereby patients exhibiting increased or decreased levels of circulating anti-Sp140 antibodies will experience a more favorable clinical outcome relative to patients with lower levels of circulating anti-Sp140 antibodies. For example, increased anti-Sp140 antibody levels are associated with the mild form of the autoimmune disease primary biliary cirrhosis (PBC), and patients with this form have a more favorable prognosis that patients with PBC who have lower levels of anti-Sp140 antibodies.

By "assaying the levels of circulating anti-Sp140 antibodies" is intended qualitatively or quantitatively measuring or estimating the levels of anti-Sp140 antibodies in a first biological sample either directly (e.g., by determining or estimating absolute anti-Sp140 antibody concentrations or titers) or relatively (e.g., by comparing the anti-Sp140 antibody levels in a first biological sample to those in a second biological sample).

Preferably, the level of anti-Sp140 antibodies in the first biological sample is measured or estimated and compared to that in a standard taken from a second biological sample obtained from an individual not having the autoimmune disease. As will be appreciated by one of ordinary skill in the art, once a standard anti-Sp140 antibody level is known, it can be used repeatedly as a standard for comparison.

By "biological sample" is intended any biological sample obtained from an individual, cell line, tissue culture, or other source which contains antibodies. Such biological samples include mammalian body fluids such as sera, plasma, urine, saliva, tears, perspiration, synovial fluid, cerebrospinal fluid and breast milk.

The present invention is useful for detecting autoimmune diseases in mammals. In particular the invention is useful during diagnosis of the of following types of autoimmune diseases in mammals: primary biliary cirrhosis, rheumatoid arthritis, systemic lupus erythematosis, Sjögren's syndrome, scleroderma and multiple sclerosis. Preferred mammals include monkeys, apes, cats, dogs, cows, pigs, horses, rabbits and humans. Particularly preferred are humans.

Assaying anti-Sp140 antibody levels in a biological sample can occur using any art-known method. Preferred for assaying anti-Sp140 antibody levels in a biological sample are immunological techniques. For example, anti-Sp140 antibody levels can be studied with classical methods such as enzyme-linked immunoadsorbent assay (ELISA), radio-immunoassay (RIA), western blot, dot/slot blot, or other similar methods employing Sp140 polypeptides or epitope-bearing fragments thereof immobilized on a solid support as described above. In this scenario, Sp140 polypeptides or epitope-bearing fragments thereof made according to the present invention are coupled to a solid support and contacted with a first biological sample to be tested for the presence of anti-Sp140 antibodies, under conditions favoring the formation of an antigen-antibody complex between the immobilized Sp140 (or fragments thereof) and anti-Sp140 antibodies. After allowing formation of the complex the anti-Sp140 antibodies that are bound to the immobilized Sp140 (if any) are detected using a second antibody directed against the anti-Sp140 antibody. The identity of this second antibody will depend upon the identity of the mammal from which the biological sample to be tested is derived; for example, if it is a human serum sample, the second antibody will be an anti-human antibody.

As an alternative approach, a "sandwich" technique may be employed. In this approach, the biological sample, or components thereof (e.g., immunoglobulins, a subset of which may include anti-Sp140 antibodies) may themselves be immobilized on a solid support as described above. These immobilized components can then be contacted with an isolated Sp140 polypeptide (or epitope-bearing fragments thereof) under conditions favoring the formation of a complex between the immobilized components and the Sp140 polypeptide. The complex is then contacted with a second antibody that binds specifically to Sp140, such as a polyclonal or monoclonal antibody made according to the present invention, and the binding of the second antibody to the complex detected with an antibody-detection system (e.g. a third antibody or an antibody-binding ligand such as protein A or protein G) by techniques well-known in the art.

To facilitate its detection, the second antibody in either of these approaches may be detectably labeled as described above. In both methods, the specific recognition is provided by the primary anti-Sp140 antibody but the secondary detection system can utilize fluorescent, enzyme, or other conjugated secondary antibodies. Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Viral Diseases and Neoplasia. It is believed that certain tissues in mammals with certain viral diseases and cancers express significantly decreased levels of the Sp140 protein and mRNA encoding the Sp140 protein when compared to a corresponding "standard" mammal, i.e., a mammal of the same species not having the viral disease or cancer. Further, it is believed that decreased levels of the Sp140 protein can be detected in certain body fluids (e.g., sera, plasma, urine, and spinal fluid) from mammals with cancer when compared to sera from mammals of the same species not having the viral disease or cancer. Thus, the invention provides a diagnostic method useful during viral disease or cancer diagnosis, which involves assaying the expression level of the gene encoding the Sp140 protein in mammalian cells or body fluid and comparing the gene expression level with a standard Sp140 gene expression level, whereby a decrease in the gene expression level over the standard is indicative of certain tumors or viral diseases.

Where a diagnosis has already been made according to conventional methods, the present invention is useful as a prognostic indicator, whereby patients exhibiting decreased Sp140 gene expression will experience a worse clinical outcome relative to patients expressing the gene at a higher level.

By "assaying the expression level of the gene encoding the Sp140 protein" is intended qualitatively or quantitatively measuring or estimating the level of the Sp140 protein or the level of the mRNA encoding the Sp140 protein in a first biological sample either directly (e.g., by determining or estimating absolute protein level or mRNA level) or relatively (e.g., by comparing to the Sp140 protein level or mRNA level in a second biological sample).

Preferably, the Sp140 protein level or mRNA level in the first biological sample is measured or estimated and compared to a standard Sp140 protein level or mRNA level, the standard being taken from a second biological sample obtained from an individual not having the viral disease or cancer. As will be appreciated in the art, once a standard Sp140 protein level or mRNA level is known, it can be used repeatedly as a standard for comparison.

Biological samples assayable according to these methods include mammalian body fluids (such as sera, plasma, urine, synovial fluid and spinal fluid) which may contain secreted Sp140 protein, and leukocyte, ovarian, prostate, heart, placenta, pancreas, liver, spleen, lung, breast and umbilical tissue which contain Sp140 protein as a component of the NB of the cells which form the tissues. Methods for obtaining tissue biopsies and body fluids from mammals are well known in the art. Where the biological sample is to include mRNA, a tissue biopsy is the preferred source.

The present invention is useful for detecting viral diseases and cancer in mammals. In particular the invention is useful for diagnosis of the of following types of cancers in mammals: leukemias; cancers of the breast, ovary, prostate, bone, liver, lung, pancreas, and spleen; sarcomas; and melanomas. Particularly suitable to detection by the methods of the present invention is acute promyelocytic leukemia (APL). The invention is also useful for diagnosis of diseases caused by the following viruses in mammals: herpes simplex virus (HSV), cytomegalovirus (CMV), human immunodeficiency virus (HIV), heptatitis virus (which may be hepatitis A, hepatitis B or hepatitis C virus), human T-cell leukemia virus-1 (HTLV-1) and adenovirus. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the Sp140 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Sp140 protein-encoding cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Sp140 protein). Northern blot analysis can be performed as described above.

Preferably, levels of mRNA encoding the Sp140 protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Sp140 protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying Sp140 protein levels in a biological sample can occur using any art-known method. Preferred for assaying Sp140 protein levels in a biological sample are antibody-based techniques. For example, Sp140 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of Sp140 protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of Sp140 protein can be accomplished using isolated Sp140 protein or fragments thereof obtained according to the present invention as a standard. This technique can also be applied to body fluids. With these samples, a molar concentration of Sp140 protein will aid to set standard values of Sp140 protein content for different body fluids, like serum, plasma, urine, spinal fluid, etc. The normal appearance of Sp140 protein amounts can then be set using values from healthy individuals, which can be compared to those obtained from a test subject.

Other antibody-based methods useful for detecting Sp140 protein gene expression include immunoassays, such as ELISA and RIA as described above. For example, a Sp140 protein-specific monoclonal antibody obtained by the methods of the present invention can be used both as an immunoadsorbent and as an enzyme-labeled probe to detect and quantify the Sp140 protein. The amount of Sp140 protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect Sp140 protein in a body fluid, in a modification of the "sandwich" assay described above. In this assay, one of the antibodies is used as the immunoadsorbent and the other as the enzyme-labeled probe.

The above techniques may be conducted essentially as a "one-step" or "two-step" assay. The "one-step" assay involves contacting Sp140 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

In addition to assaying Sp140 protein levels in a biological sample obtained from an individual, Sp140 protein can also be detected in vivo by imaging. Antibody labels or markers for in vivo imaging of Sp140 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A Sp140 protein-specific antibody or antibody fragment, such as that provided by the present invention, which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer or viral disease. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain Sp140 protein. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer,* S. W. Burchiel and B. A. Rhodes, eds., Masson Publishing Inc. (1982)).

Disease Therapy

In addition to their use in disease diagnosis and prognosis, the Sp140 protein and fragments thereof may be used in therapeutic regimens for treating mammals afflicted with certain diseases. Particularly amenable to such an approach are those diseases that are characterized by decreased levels of Sp140 protein expression in the tissues of a mammal suffering from the disease, and which are responsive to treatments which increase the expression of Sp140 protein intracellularly. Diseases that are particularly treatable by these methods include leukemias; cancers of the breast, ovary, prostate, bone, liver, lung, pancreas, and spleen; sarcomas; and melanomas. Particularly suitable to treatment by the methods of the present invention is acute promyelocytic leukemia (APL). The invention is also useful for treatment of diseases caused by the following viruses in mammals: herpes simplex virus (HSV), cytomegalovirus (CMV), human immunodeficiency virus (HIV), hepatitis virus (including hepatitis A, hepatitis B and hepatitis C viruses), human T-cell leukemia virus-1 (HTLV-1) and adenovirus. Preferred mammals for treatment include monkeys, apes, cats, dogs, cows, pigs, horses, rabbits and humans. Particularly preferred are humans.

A mammal suffering from such a disease is preferably treated by gene therapy. In this approach, the isolated nucleic acid molecule depicted in FIG. 2A (SEQ ID NO:1), a nucleic acid molecule encoding an Sp140 protein or a fragment thereof depicted in FIG. 2A (SEQ ID NO:2), or a nucleic acid molecule complementary to those described above, is incorporated into a vector suitable for introducing the nucleic acid molecule into cells of the mammal to be treated, to form a transfection vector. Suitable vectors for this purpose include retroviruses and adenoviruses. Techniques for the formation of the transfection vector comprising the Sp140-encoding nucleic acid molecule are well-known in the art, and are generally described in "Working Toward Human Gene Therapy," Chapter 28 in *Recombinant DNA, 2nd Ed.,* Watson, J. D. et al., eds., New York: Scientific American Books, pp. 567–581 (1992), and in the references cited therein.

By undertaking this approach, the level of Sp140 protein expression is increased in the NBs of the cells of the animal being treated, thereby reversing the effects of the virus or cancer and either curing the disease, or inducing a remission or an alleviation of the symptoms thereof. Analogous gene therapy approaches have proven effective or to have promise in the treatment of other mammalian diseases such as cystic fibrosis (Drumm, M. L. et al., *Cell* 62:1227–1233 (1990); Gregory, R. J. et al., *Nature* 347:358–363 (1990); Rich, D. P. et al., *Nature* 347:358–363 (1990)), Gaucher disease (Sorge, J. et al., *Proc. Natl. Acad. Sci. USA* 84:906–909 (1987); Fink, J. K. et al., *Proc. Natl. Acad. Sci. USA* 87:2334–2338 (1990)), certain forms of hemophilia (Bontempo, F. A. et al., *Blood* 69:1721–1724 (1987); Palmer, T. D. et al., *Blood* 73:438–445 (1989); Axelrod, J. H. et al., *Proc. Natl. Acad. Sci. USA* 87:5173–5177 (1990); Armentano, D. et al., *Proc. Natl. Acad. Sci. USA* 87:6141–6145 (1990)) and muscular dystrophy (Partridge, T. A. et al., *Nature* 337:176–179 (1989); Law, P. K. et al., *Lancet* 336:114–115 (1990); Morgan, J. E. et al., *J. Cell Biol.* 111:2437–2449 (1990)), as well as in the treatment of certain cancers such as metastatic melanoma Rosenberg, S. A. et al., *Science* 233:1318–1321 (1986); Rosenberg, S. A. et al., *N. Eng. J. Med.* 319:1676–1680 (1988); Rosenberg, S. A. et al., *N. Eng. J. Med.* 323:570–578 (1990)).

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Materials and Methods

Unless otherwise indicated, the following materials and methods were generally used in the Examples.

Human serum. Serum was obtained from a patient with PBC. The diagnosis was based on the presence of elevated liver function enzymes and high titer antibodies directed against the mitochondrial antigen E2-pyruvate dehydrogenase complex (Kaplan, M. M., *N. Eng. J. Med.* 316:521–528 (1987)).

Cell culture and induction of differentiation. HL60 cells (American Type Tissue Collection, Rockville, Md.) and NB4 cells (a gift of M. Lanotte, Institut National de la Sante et Recherche Medicale, Paris, France) were maintained in RPMI-1640 (GIBCO/LTI; Gaithersburg, Md.) supplemented with 10% fetal bovine serum, L-glutamine (2 mM), penicillin (200 U/ml) and streptomycin (200 $\mu$g/ml).

Differentiation of HL60 cells toward monocytes was induced by the addition of phorbol-12, 13-myristate acetate (PMA; $2\times10^{-4}$ M; Sigma Chemical Co., St. Louis, Mo.), while their differentiation toward polymorphonuclear leukocytes was induced by incubation with dimethylsulfoxide (DMSO; 1.2%; Sigma Chemical Co., St. Louis, Mo.) (Collins, S. J., *Blood* 70:1233–1244 (1987); Collins, S. J. et al., *Proc. Natl. Acad. Sci. (USA)* 75:2458–2462 (1978)). The effect of IFN on the expression of Sp140 in HL60 cells was studied by incubating these cells in the presence of IFN$\gamma$ (200 U/ml). Differentiation of NB4 cells was induced by treatment for 5 days with 1 $\mu$M all-trans retinoic acid (RA) (Lanotte, M. et al., *Blood* 77:1080–1086 (1991)).

Immunohistochemical staining. Adherent cells were grown in tissue culture chambers (Nunc, Inc., Naperville, Ill.) and fixed in 4% paraformaldehyde in phosphate-buffered saline (PBS) at room temperature for 15 minutes. Cytospin preparation of nonadherent cells was performed with 50,000 cells at 500 rpm for 5 minutes followed by air drying and fixation in paraformaldehyde. Prior to incubation with antibodies, cells were permeabilized for about five minutes with 0.1% saponin in PBS and then briefly treated with 0.6% hydrogen peroxide in 60% methanol to block endogenous peroxidase activity. Cells were immunostained with mouse monoclonal antibody directed against PML (a gift of K. van Der Kraan, E. C. Slater Instituut, Amsterdam; (Stuurman, N. et al., *J. Cell Sci.* 101:773–784 (1992))) or rat antiserum directed against Sp140 using horseradish peroxidase (HRP)-conjugated avidin-biotin complexes (ABC) (Vector ABC Elite Kit; Vector Laboratories, Burlingame, Calif.), according to standard procedures. In some experiments, cells were stained with rat anti-Sp140 antibodies that were affinity-purified using recombinant Sp140 protein (see below). Cells incubated with mouse monoclonal antibody and biotinylated goat anti-mouse IgG antiserum were subsequently exposed to either TruBlue peroxidase substrate (Kirkegaard and Perry Laboratories, Inc., Gaithersburg, Md.) which resulted in blue staining, or to 3-3'diaminobenzimide (DAB) which produced a brown precipitate, according to manufacturer's instructions. Similarly, cells incubated with rat anti-SP140 antiserum and biotinylated goat anti-rat IgG antiserum were treated with either TruBlue peroxidase substrate or DAB. Control studies included immunostaining with pre-immune rat serum and anti-Sp140 antibodies pre-absorbed with recombinant protein (see below). Double immunostaining reactions were used to determine the cellular location of Sp140 relative to PML. Horseradish peroxidase-conjugated ABC and DAB (brown chromagen) were used to detect PML, and alkaline phosphatase-conjugated ABC and PhThalo Blue (Kirkegaarde and Perry Laboratories, Inc.) were used to detect Sp140.

Isolation and preliminary analysis of cDNA clones. Patient serum diluted 1:200 in blocking solution (PBS containing 5% nonfat dry milk, pH 7.4) was used to screen a λgt11 cDNA expression library prepared from HepG2 (human hepatocellular carcinoma) cells (Clontech Laboratories, Palo Alto, Calif.) (Young, R. A., and Davis, R. W., Science 222:778–782 (1983)). One clone expressing immunoreactive protein was isolated from approximately one million bacteriophages. The cDNA clone (Sp140. 1) was radiolabelled and used to screen a λgt10 human umbilical vein endothelial cell (HUVEC) cDNA library (Staunton, D. E. et al., Cell 52:925–933 (1988)). One positive clone (Sp140.2) was identified. Amplification of the 5'end of the cDNA encoding Sp140 was performed using the 5'RACE system (Life Technologies, Inc., Grand Island, N.Y.) (Frohman, M. A. et al., Proc. Natl. Acad. Sci. (USA) 85:8998–9002 (1988)) and cDNA prepared from human placenta (Clontech Laboratories). The first PCR reaction used an 18-nucleotide primer (GSP1: 5'-CCTGAGGCACTGCTATAT-3') (SEQ ID NO:7) and the anchor primer supplied by the manufacturer. A second, "nested" oligonucleotide with a 5' EcoRI site (GSP2: 5-CGGAATTCGAAATGGCCTTGTTATTG-3') (SEQ ID NO:8) was used with a second anchor primer (modified to include an EcoRI site) to further amplify the product. The PCR product was treated with EcoRI and ligated into pUC19. The nucleotide sequences of the cDNAs and two independent 5'RACE products were determined by the dideoxy chain termination method (Sanger, F., Science 214:1205–1210 (1981)).

In Vitro Transcription and Translation of Sp140. To create a full-length cDNA encoding Sp140, a KpnI/BstYI fragment of the 5'RACE product and a BstYI/EcoRI fragment of cDNA Sp140.2 were ligated into the KpnI and EcoRI sites in eukaryotic expression vector pcDNA3 (Invitrogen Corp., San Diego, Calif.) to create plasmid pcDNA3-Sp140. The plasmid was used in the TnT Reticulocyte Lysate System (Promega Corp., Madison, Wis.) to produce in vitro-translated protein.

Production of rat antiserum. Male Sprague-Dawley rats were immunized with recombinant protein containing Sp140 amino acids 131–391 fused to glutathione-S-transferase (GST). The plasmid encoding this portion of Sp140 was prepared by ligating cDNA Sp140.1 into the EcoRI site of the prokaryotic expression vector pGEX (Pharmacia, Piscataway, N.J.). The plasmid was used to transform E. coli, and expression of the fusion protein was induced by treatment with IPTG. The 110-kDa fusion protein was purified from E. coli proteins as described by Smith and Johnson (Smith, D. B., and Johnson, K. S., Gene 67:31–40 (1988)). Primary immunization of three rats was performed using 50 µg of purified protein emulsified in complete Freund's adjuvant (CFA) for each animal. Two subsequent booster injections consisting of 50 µg of protein were given at 2 week intervals.

Rat antibodies directed against Sp140 were affinity-purified using nitrocellulose-bound recombinant protein as described previously (Olmsted, J. B., J. Biol. Chem. 256:11955–11957 (1981)). The GST-Sp140 (131–391) fusion protein was fractionated by SDS-PAGE and transferred to nitrocellulose as described below. The membrane was incubated in blocking solution for 1 h at room temperature and was then incubated with rat antiserum diluted 1:10 in blocking solution. Bound antibodies were eluted by treatment with 100 mM glycine-HCl (pH 2.5) for 10 minutes at room temperature. The antibody solution was neutralized by addition of 1 M Tris-buffer (pH 8.8). Affinity-purified antibodies were concentrated using an Amicon concentrator (W. R. Grace and Co., Beverly, Mass.).

To confirm the specificity of anti-Sp140 antibodies, rat antiserum (or affinity-purified anti-Sp140 antibodies) were pre-incubated with 1 µg of purified, recombinant protein for 1 hour at room temperature prior to use in immunoblot or immunohistochemistry.

SDS-PAGE and immunoblotting. DMSO-treated HL60 cells were lysed in cold PBS containing PMSF (1 mM), leupeptin (2 µM) and pepstatin A (1 µM). DMSO-treated HL60 cell lysates or reticulocyte lysates containing in vitro-translated protein were boiled for five minutes in sample buffer (0.125 M tris-HCl, 4% SDS, 20% glycerol, and 10% β-mercaptoethanol). Proteins were fractionated by 8% SDS-PAGE according to the method of Laemmli (Laemmli, U. K., Nature (London), 227:680–685 (1970)) and electroblotted onto nitrocellulose membranes (Towbin, H. et al., Proc. Natl. Acad. Sci. (USA) 76:4350 4354 (1979)). Membranes were incubated in blocking solution at room temperature for 1 h and were then incubated in human serum diluted 1:1000 in blocking solution. Bound antibodies were visualized by incubation with HRP-conjugated protein A (Amersham, Arlington Heights, Ill.) and enhanced chemiluminescence (Amersham). For studies using rat antiserum, membranes were incubated for 1 hour at room temperature in antiserum diluted 1:1000 in blocking solution. Bound antibodies were detected using HRP-conjugated goat anti-rat antiserum (Amersham) and chemiluminscence, according to manufacturer's instructions.

RNA blot hybridization. The level of mRNA encoding Sp140 in human tissues was determined by hybridizing membranes contained 2.5 µg of poly(A)+-selected RNA from human tissues (multiple Tissue Northern Blots, Clontech Laboratories) with a $^{32}$P-radiolabelled SacI-EcoRI fragment of Sp140 (bp 2,089–2,905). Membranes were washed under stringent conditions and were exposed to autoradiography for 9 hours. To confirm the presence of poly (A)+-selected RNA in each lane, the membranes were hybridized with a $^{32}$P-radiolabeled β-actin cDNA. The membranes were washed under stringent conditions and exposed to autoradiography for 30 minutes.

RNA was extracted from human cell lines using the guanidium isothiocyanate/cesium chloride method (Sambrook, J. et al., Molecular Cloning: A Laboratory Manual, Cold Spring Harbor Laboratory Press, Cold Spring Harbor, N.Y. (1989)). RNA was fractionated in formaldehyde-agarose gels (10 µg/lane) and transferred to nylon membranes. Membranes were hybridized with the radiolabelled SacI/EcoRI restriction fragment of the Sp140 cDNA. Membranes were washed and subjected to autoradiography. To confirm comparable loading of RNA in each lane, membranes were hybridized with a 10-fold molar excess of a $^{32}$P-radiolabeled oligonucleotide complementary to rat 18S RNA (Lee, R. T. et al., J. Clin. Invest. 81:431–434 (1988)).

Example 1

Isolation of a cDNA encoding Sp140

Patients with the autoimmune disease PBC produce autoantibodies directed against proteins in the nuclear body. To identify novel components of this structure, serum from a patient with PBC was used to screen a λgt11 cDNA expression library prepared from HepG2 cells. Among approximately one million bacteriophages, one clone (Sp140.1) producing immunoreactive recombinant protein was identified. The nucleotide sequence of the cDNA was found to contain a 781-base pair (bp) open reading frame (ORF) that extended for the entire length of the fragment, suggesting that the cDNA encoded only a portion of a protein. To identify a full-length cDNA, the DNA fragment was radiolabelled and used to rescreen the HEpG2 cDNA library; no additional clones were identified. The radiolabelled fragment was then used to screen a HUVEC cDNA library and a single hybridizing cDNA (Sp140.2) was identified among one million bacteriophages. The clone contained a 2,732-bp insert that included the entire length of Sp140.1. A 2,193-nucleotide ORF extended to the 5' end of Sp140.2, suggesting that this clone also encoded only part of the full-length protein. The 5'RACE technique (Frohman, M. A. et al., *Proc. Natl. Acad. Sci. (USA)* 85:8998–9002 (1988)) was used to identify the 5' end of the mRNA encoding Sp140. The RACE product contained an additional 173-bp segment. The PCR product and the 5' end of Sp140.2 were joined at a BstYI site, and the resultant full-length cDNA was ligated into the eukaryotic expression vector pcDNA3.

To confirm that the isolated cDNA encoded a protein that reacted with autoantibodies in the patient's serum, the plasmid was used for in vitro transcription and translation of Sp140. Autoantibodies in the patient's serum reacted with the 140-kDa translation product by immunoblot (FIG. 1, panel A, "+" lane). In contrast, this band was not detected in a lane containing reticulocyte lysate proteins alone (FIG. 1, panel A, "−" lane). These results demonstrate that pcDNA3-Sp140 encodes a protein that is immunoreactive with autoantibodies from a patient with the autoimmune disease PBC.

Example 2

Sequence Analysis of Sp140

Upon analysis of its nucleotide sequence, the cDNA encoding Sp140 isolated in Example 1 was found to be 2,905 bp in length and to contain an ORF from bp 107 to 2,365 FIG. 2A; SEQ ID NO:1). The start codon is preceded by an in-frame stop codon. In preliminary analyses, several features of the predicted amino acid sequence of Sp140 (SEQ ID NO:2) were of interest. First, as shown in FIG. 2B, the amino terminal portion of Sp140 between amino acids 29–157 (SEQ ID NO:3) is 49% identical to the amino terminal region of Sp100 (SEQ ID NO:4), a previously identified autoantigen within the NB. In addition, the region in Sp140 between amino acids 228–317 is strongly negatively charged, in that 29 of the 92 amino acids in this region are either glutamic or aspartic acid. The central portion of Sp140, between amino acids 381–400, contains a potential bi-partite nuclear localization sequence (Silver, P. A., *Cell* 64:489–497 (1991); Dingwall, C., and Laskey, R. A., *TIBS* 16:478–481 (1991); Robbins, J. et al., *Cell* 64:615–623 (1991)). The carboxyl portion of Sp140 contains a cysteine-rich, zinc finger motif (amino acids 579–639), followed by a segment (amino acids 681–715; SEQ ID NO:5) that is similar to the bromodomain in *Saccharomyces cerevisiae* protein BDF1 (SEQ ID NO:6) (FIG. 2C) (Tamkun, J. W. et al., *Cell* 68:561–572 (1992); Haynes, S. R. et al., *Nucl. Acids Res.* 20:2603 (1992); Lygerou, Z. et al., *Nucleic Acids Res.* 22:5332–5340 (1994)). The presence of a strongly negatively charged region, zinc finger motif and bromodomain suggests that Sp140 may be involved in the regulation of gene transcription.

Example 3

Expression of Sp140 in Human Tissues and Cell Lines

To determine its tissue distribution, the expression of the gene encoding Sp140 in human tissues was analyzed by RNA blot hybridization. High levels of Sp140 mRNA were detected in human spleen and peripheral blood leukocytes (FIG. 3). In contrast, much lower levels of Sp140 mRNA were observed in thymus, prostate, ovary, small intestine, and colon. Low levels of a slightly smaller transcript, possibly an alternatively spliced form of Sp140 mRNA, were detected in several tissues. In addition, a 1,200-nt transcript of uncertain significance was detected in human testis. Very low levels of Sp140 mRNA were observed in human heart, brain, placenta, lung, liver, skeletal muscle, kidney and pancreas (data not shown).

To investigate the expression of Sp140 in cells of the monocyte/granulocyte lineage, RNA was prepared from the myeloid precursor cell lines HL60 and NB4 before and after induction of cellular differentiation. Treatment of HL60 cells with DMSO induces a polymorphonuclear leukocyte morphology; treatment with phorbol-12, 13 myristate acetate (PMA) induces a monocyte-like morphology (Collins, S. J., *Blood* 70:1233–1244 (1987); Collins, S. J. et al., *Proc. Natl. Acad. Sci. (USA)* 75:2458–2462 (1978)). Low levels of Sp140 mRNA were detected in untreated HL60 cells (FIG. 4, lanes 1 and 4). The level of mRNA was increased by treatment of HL60 cells with either PMA (FIG. 4, lane 2) or DMSO (FIG. 4, lane 5).

Treatment of the human APL cell line NB4 with all-trans retinoic acid (RA) is also associated with cellular differentiation (Lanotte, M. et al., *Blood* 77:1080–1086 (1991)). Low levels of Sp140 mRNA were detected in NB4 cells prior to treatment with RA (FIG. 4, lane 7). In contrast, five days after addition of RA, the level of Sp140 mRNA was markedly increased (lane 8). These results demonstrated that differentiation of HL60 and NB4 cells is associated with increased expression of Sp140.

Example 4

IFN Induction of the Expression of Sp140

It has been previously shown that the expression of certain components of the NB is enhanced by treatment of cells with IFN (Ascoli, C. A., and Maul, G. G., *J. Cell. Biol.* 112:785–795 (1991); Koken, M. H. M. et al., *Oncogene* 10:1315–1324 (1995); Guldner, H. H. et al., *J. Immunol.* 149:4067–4073 (1992); Doucas, V. et al., *Genes & Devel.* 10:196–207 (1996)). To investigate the effect of IFN on the level of Sp140 mRNA, HL60 cells were treated with IFNγ and Sp140 mRNA levels determined by northern blotting. As shown in FIG. 5, increased Sp140 mRNA levels were detected 24 hours after treatment and persisted for at least four days. In addition, treatment with IFNγ further increased Sp140 mRNA in cells treated with PMA (FIG. 4, lane 3) or DMSO (FIG. 4, lane 6). These results demonstrate that, as has been reported for Sp100, NDP52 and PML, the expression of Sp140 is increased upon treatment of cells with IFNγ.

Example 5

Cellular Localization of Sp140

To permit cellular localization of Sp140 by immunohistochemical techniques, antiserum directed against a recombinant fragment of the protein was prepared. Three rats were immunized with Sp140 amino acids 131–391 fused to GST (GST-Sp140[131–391]). The resulting antisera reacted with the in vitro translation product of pcDNA3-Sp140 (FIG. 1B, "+" lane). In addition, the antisera reacted with a 140-kDa band in an immunoblot prepared from DMSO-treated HL60 cells (FIG. 6, lane 1). Pre-treatment of rat antiserum with recombinant GST-Sp140 (131–391) blocked reactivity with the 140-kDa protein (FIG. 6, lane 2). These results demonstrate that rat antiserum reacts with Sp140. Although the region of Sp140 used to immunize rats contained a short segment that was similar to Sp100 (9 of 27 amino acids identical), the rat antiserum did not react with Sp100 by immunoblot. In addition, rat antiserum did not stain NBs in HEp2 cells, a cell line that contains high levels of Sp100, but only very low levels of Sp140 (data not shown). These findings indicate that the rat antisera raised against human Sp140 specifically bind to Sp140 and do not recognize Sp100.

To determine the cellular location of Sp140, affinity-purified rat anti-Sp140 antibodies were prepared and used to stain DMSO-treated HL60 cells. Antibodies reacted with 5–20 punctate structures in the nucleus of these cells (FIG. 7, panel A). This is the same pattern as that produced by mouse monoclonal antibodies directed against PML (FIG. 7, panel B). Pre-treatment of rat anti-Sp140 antibodies with recombinant Sp140 protein completely blocked the NB staining pattern (FIG. 7, panel C). Two color immunohistochemistry demonstrated that rat anti-Sp140 antibodies and mouse anti-PML antibodies localized to the same structures in individual cells (FIG. 7, panel D).

To investigate the cellular distribution of Sp140 in APL cell line NB4, rat antiserum was used to stain NB4 cells before and after treatment with RA. Rat antiserum directed against Sp140 stained NBs in NB4 cells that were treated for 5 days with RA (FIG. 7, panel E). Mouse monoclonal antibodies directed against PML produced the same pattern of staining in RA-treated NB4 cells (FIG. 7, panel F). Rat anti-Sp140 antiserum did not stain the nuclei of untreated NB4 cells (FIG. 7, panel G). Taken together, these results indicate that Sp140 is a component of the NB.

General Discussion

Cloning and characterization of Sp140. Patients with the autoimmune disease primary biliary cirrhosis (PBC) produce antibodies directed against components of a cellular organelle known as the nuclear body (NB). Three proteins in the NB—Sp100, NDP52 and PML—have previously been shown to be targets of autoantibodies. In the present invention, serum from a patient with PBC was used to identify a novel NB antigen which was designated Sp140 (SEQ ID NOs: 1, 2). The amino terminal portion of Sp140 (SEQ ID NO:3) is 49% identical to the amino terminal region of Sp100 (SEQ ID NO:4). These portions of Sp100 and Sp140 contain potential coiled coil motifs (data not shown). It has been hypothesized that the amino terminal domain of Sp100 may be a likely region for interactions between Sp100 and "other PBC autoantigens" (Koken, M. H. M. et al., *EMBO J.* 13:1073–1083 (1994)). A direct interaction between Sp100 and Sp140, however, has not yet been demonstrated.

The region in Sp140 between amino acids 579–619 contains a cysteine-rich, zinc finger motif. The presence of a zinc finger domain in Sp140 suggests that the protein is a member of a larger family of proteins that have been implicated in the control of development, cellular differentiation and cell growth. The zinc finger region may bind DNA directly or may interact with a second protein to form a dimer that binds DNA (Schleif, R., *Science* 241:1182–1187 (1988); Struhl, K., *TIBS* 14:137–140 (1989); Freemont, P. S., *Ann. NY Acad. Sci.* 684:174–12 (1993)). The order of the cysteine/histidine residues in Sp140 (C4HC3) differs slightly from that of the previously described RING finger (C3HC4) and LIM motifs (C2HC5). Koken et al. have observed that the C4HC3 motif is present in a variety of proteins including Drosophila trithorax and its human homologue ALL-1 and have proposed the name TTC (for trithorax consensus) for this family of proteins (Koken, M. H. M. et al., *Comptes Rend. Ser. III* 318:733–739 (1995)).

The portion of Sp140 between amino acids 681–715 (SEQ ID NO:5) contains a bromodomain. Bromodomains are conserved sequences that are found in a variety of transcriptional regulatory proteins (Tamkun, J. W. et al., *Cell* 68:561–572 (1992); Haynes, S. R. et al., *Nucl. Acids Res.* 20:2603 (1992); Lygerou, Z. et al., *Nucleic Acids Res.* 22:5332–5340 (1994)). The predicted secondary structure of the bromodomain includes two strongly amphipathic α helices followed by reverse turns. Although the functional significance of the bromodomain is unknown, the hydrophobic surfaces of the α helices may serve as sites of intramolecular protein-protein interaction. These interactions may influence the assembly or activity of multicomponent complexes involved in transcriptional activation (Carlson, M., and Laurent, B. C., *Curr. Opin. Cell. Biol.* 6:396–402 (1994)).

Expression of Sp140 in human tissues and cell lines. Also of interest is the tissue-specific expression of Sp140. Specifically, high levels of mRNA encoding Sp140 were detected in human spleen and peripheral blood leukocytes and much lower levels were detected in all other tissues examined. Its predominant expression in human leukocytes suggests that Sp140 may have an important role in cellular functions that are unique to these cells. Low levels of Sp140 mRNA were detected in the myeloid precursor cell lines HL60 and NB4, while the expression of Sp140 was markedly increased during the course of differentiation of HL60 cells toward either monocytes or polymorphonuclear leukocytes and expression of Sp140 in NB4 cells was markedly increased following treatment with RA which induces a polymorphonuclear leukocyte morphology. These results suggest that Sp140 may have a role in the differentiation of myeloid precursor cells.

The expression of Sp140 was not limited to leukocytes belonging to the monocyte/granulocyte lineage. For example, Sp140 mRNA was also detected in the T cell line Hut78 and in the B cell line Raji. In contrast, however, Sp140 was not expressed in the T cell line Jurkat nor in the B cell lines Ramos and HS-Sultan (data not shown). The significance of Sp140 expression in some, but not all, lymphocyte cell lines is not yet fully understood.

Sp140 and acute promyelocytic leukemia (APL). In APL, a translocation between chromosomes 15 and 17 results in fusion of the NB protein PML to RARα. Expression of the fusion protein disrupts the NB and inhibits normal myeloid maturation. Treatment of APL cells with RA results in reformation of the NB and induces leukemic cell maturation (Dyck, J. A. et al., *Cell* 76:333–343 (1994); de The, H. et al., *Nature* (*London*) 347:558–561 (1990); Borrow, J. et al., *Science* 249:1577–1580(1990); Longo, L. et al., *J. Exp. Med.* 172:1571–1575 (1990); Kakizuka, A. et al., *Cell* 66:663–674 (1991); Weis, K. et al., *Cell* 76:345–356 (1994); Koken, M. H. M. et al., *EMBO* 13:1073–1083 (1994)). The mechanism of action of RA in these cells is unknown. The myeloid precursor cell line NB4 contains the t(15; 17) translocation associated with APL (Lanotte, M. et al., *Blood* 77:1080–1086 (1991)). Using immunohistochemistry, Sp140 was not detected in untreated NB4 cells (FIG. 7, panel G). This was not surprising in view of the low level of Sp140 mRNA in these cells (FIG. 4). However, following treatment of NB4 cells with RA, Sp140 was detected within the NBs of these cells (FIG. 7, panel E). Taken together, the observations that expression of Sp140 in NB4 cells is induced by RA treatment and that Sp140 associates with the NB suggest that Sp140 may have a role in the action of RA on APL cells. The observed resistance of APL cells to RA that develops over time (Ruchaud, S. et al., *Proc. Natl. Acad. Sci.* (*USA*) 91:8428–8432 (1994); Warrell, R. P., *Blood* 82:1949–1953 (1993)) may, in part, be a result of a second event in these cells that alters the structure or function of a protein (possibly Sp140) that interacts with PML in the NB.

Sp140 and viral infection. IFN treatment increases the expression of each of the previously identified components of the NB (Sp100, PML and NDP52). This IFN induction of NB-associated proteins may have functional significance. For example, Sp100 may be involved in establishing an "anti-viral state" (Guldner, H. H. et al., *J. Immunol.* 149:4067–4073 (1992)), and it has recently been demonstrated that overexpression of PML in Hep2 cells dramatically decreases the ability of these cells to support adenoviral replication (Doucas, V. et al., *Genes & Devel.* 10:196–207 (1996)). Based on these results, it has been hypothesized that increased expression of PML may delay or block Sp100 and NDP52 recruitment to viral replication domains resulting in inhibition of viral DNA replication (Doucas, V. et al., *Genes & Devel.* 10:196–207 (1996)). The identification in the present invention of Sp140, a novel NB component that is expressed in cells involved in host defense, raises the possibility that Sp140, like other NB components, may have a role in the pathogenesis of, or the host response to, viral infection.

In summary, a novel component of the NB has been identified and characterized. The predicted amino acid sequence of Sp140 suggests that this protein is involved in the regulation of gene transcription. The predominant expression of Sp140 in leukocytes indicates that this protein has an important role in cellular functions that are unique to these cells.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated nucleic acid molecule comprising a polynucleotide having a nucleotide sequence selected from the group consisting of:
   (a) the nucleotide sequence set forth in SEQ ID NO:1; and
   (b) a nucleotide sequence encoding the Sp140 polypeptide having the amino acid sequence set forth in SEQ ID NO:2.

2. The nucleic acid molecule of claim 1 wherein said polynucleotide has the complete nucleotide sequence set forth in SEQ ID NO:1.

3. A method for making a recombinant vector comprising inserting the isolated nucleic acid molecule of claim 1 into a vector.

4. A recombinant vector produced by the method of claim 3.

5. A method of making a recombinant host cell comprising introducing the recombinant vector of claim 4 into a host cell.

6. A recombinant host cell produced by the method of claim 5.

7. A recombinant method for producing a Sp140 polypeptide, said method comprising culturing the recombinant host cell of claim 6 under conditions such that said polypeptide is expressed and recovering said polypeptide.

* * * * *